United States Patent [19]
Hirai et al.

[11] Patent Number: 4,983,751
[45] Date of Patent: Jan. 8, 1991

[54] OXAZOLIDINEDIONE DERIVATIVES, METHOD OF PRODUCING THE DERIVATIVES, AND HERBICIDES CONTAINING THE DERIVATIVES

[75] Inventors: Kenji Hirai; Takamasa Futikami; Atsuko Murata, all of Kanagawa; Hiroaki Hirose; Masahiro Yokota, both of Chiba; Shoin Nagato, Tokyo, all of Japan

[73] Assignees: Sagami Chemical Research Center; Chisso Corporation; Kaken Pharmaceutical Co. Ltd., Japan; a part interest

[21] Appl. No.: 345,369

[22] Filed: Jan. 31, 1989

Related U.S. Application Data

[62] Division of Ser. No. 72,268, Jun. 11, 1987, Pat. No. 4,818,272.

[30] Foreign Application Priority Data

Oct. 11, 1985 [JP] Japan .................. 60-226270
Oct. 11, 1985 [JP] Japan .................. 60-226294

[51] Int. Cl.$^5$ ............................. C07C 69/96
[52] U.S. Cl. ................................... 558/272
[58] Field of Search ......................... 558/272

[56] References Cited

U.S. PATENT DOCUMENTS 2,917,534 12/1959 Sims et al. ................. 558/272
3,322,812 5/1967 Brotherton et al. ........ 558/272
3,505,384 4/1970 Krimm et al. ............... 558/272

*Primary Examiner*—Werren B. Lone
*Attorney, Agent, or Firm*—Nixon & Vanderhye

[57] ABSTRACT

Disclosed are novel oxazolidinedione derivatives expressed by the following formula:

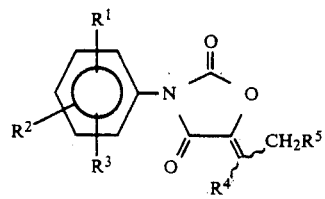

($R^1$, $R^2$, $R^3$, $R^4$ and $R^5$ being defined in the specification), a method of producing the derivatives and herbicides containing the derivatives as an active ingredient. Carbonate esters which are intermediates in the method of producing the oxazolidinedione derivatives are also disclosed.

These novel derivatives exhibit excellent weed-killing activity for harmful weeds and low phytotoxicity for crops.

1 Claim, No Drawings

OXAZOLIDINEDIONE DERIVATIVES, METHOD OF PRODUCING THE DERIVATIVES, AND HERBICIDES CONTAINING THE DERIVATIVES

This is a division of application Ser. No. 07/072,268, filed June 11, 1987, U.S. Pat. No. 4,818,272.

DETAILED DESCRIPTION OF THE INVENTION

1. Field of the Invention

The present invention relates to oxazolidinedione derivatives and a production method thereof, and particularly to oxazolidinedione derivatives expressed by the following formula:

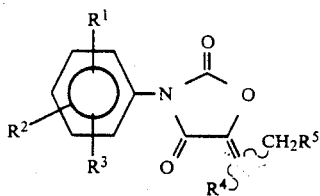

(wherein $R^1$, $R^2$ and $R^3$ independently denote hydrogen atoms, halogen atoms, nitro groups, alkyl groups, alkoxyl groups, alkenyloxy groups, alkynyloxy groups or cycloalkyloxy groups; $R^4$ and $R^5$ independently denote hydrogen atoms, alkyl groups or aryl groups or may be combined with each other to form a polymethylene chain; and the above-described alkyl groups, alkoxyl groups, alkenyloxy groups, alkynyloxy groups, cycloalkyloxy groups and aryl groups may be substituted), a production method thereof and herbicides containing the derivatives as an active ingredient.

Various derivatives having substituents at the 5-positions of oxazolidinedione rings have been known, but oxazolidinedione derivatives having methylidene groups at the 5-positions have not been reported at all because of difficulty in the synthesis thereof.

In addition, although many heterocyclic compounds having a weed-killing activity have previously been synthesized and put to practical use, no practical oxazolidinedione derivative having weed-killing activity has previously

Problems to be Solved by the Invention

It is an object of the present invention to provide novel compounds having high selectivity for weeds and powerful weed-killing activity and to provide an industrial method of producing compounds and herbicides containing these compounds as an active ingredient.

Means for Solving the Problems

The inventors have found that vigorous weed-killing activity and high selectivity for various weeds may be imparted to herbicides by introducing methylidene groups having various substituents at the 5-positions of oxazolidinedione derivatives.

The target compounds of the present invention are shown by the formula (I), wherein $R^1$, $R^2$ and $R^3$ independently denote hydrogen atoms; nitro groups; halogen atoms such as fluorine, chlorine, bromine and iodine atoms; straight or branched chain alkyl groups having 1 to 8 carbon atoms, preferably 1 to 5 carbon atoms, such as methyl, ethyl, n-propyl, isopropyl, n-butyl, n-pentyl, n-hexyl, n-heptyl, and n-octyl groups which may be substituted by one or more halogen atoms; alkoxyl groups having 1 to 18 carbon atoms, preferably 1 to 8 carbon atoms, such as methoxyl, ethoxyl, n-propoxyl, isopropoxyl, n-butoxyl, t-butoxyl groups which may be substituted by one or more alkoxy-carbonyl groups (2 to 18 carbon atoms) or halogen atoms: cycloalkoxyl groups having 3 to 12 carbon atoms, preferably 3 to 8 carbon atoms, such as cyclohexyloxy, cyclopentyloxy, and cyclopropyloxy groups which may be substituted by one or more lower alkyl groups (1 to 5 carbon atoms) or halogen atoms; straight or branched chain alkenyl groups having 2 to 12 carbon atoms, preferably 2 to 8 carbon atoms, such as allyl, methyllyl, propenyl, butenyl, pentenyl and hexenyl groups which may be substituted by one or more halogen atoms; or straight or branched chain alkynyl groups having 2 to 12 carbon atoms, preferably 2 to 8 carbon atoms, such as propargyl, 1-methylpropargyl, 1,1-dimethylpropargyl, 2-butynyl, 3-butynyl, 2-pentynyl, 3-pentynyl groups which may be substituted by one or more halogen atoms; and $R^4$ and $R^5$ independently denote hydrogen atoms, straight or branched chain alkyl groups having 1 to 18 carbon atoms, preferably 1 to 8 carbon atoms, such as methyl, ethyl, n-propyl, isopropyl, n-butyl, isobutyl, n-hexyl, and n-octyl which may be substituted by one or more halogen atoms; aryl groups having 6 to 10 carbon atoms such as phenyl, p-chlorophenyl, p-fluorophenyl, m, p-dimethoxyphenyl, and p-methylphenyl which may be substituted by halogen atoms or lower alkyl groups having 1 to 3 carbon atoms; or $R^4$ and $R^5$ may be combined with each other to form a straight or branched chain polymethylene group having 3 to 10 carbon atoms.

The position at which $R^1$, $R^2$ and $R^3$ are bonded to the phenyl group is not particularly limited, but when two of $R^1$ to $R^3$ are other than hydrogen atoms, 2, 4-, 2, 5-, 3, 4- or 3, 5-position is preferable, and when all three groups are other than hydrogen atoms, 2, 4, 5- or 2, 4, 6-position is preferable.

Typical examples of compounds expressed by the formula (I) are shown in Table 1.

TABLE 1

Oxazolidinedione Derivatives[1]

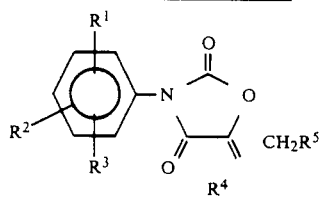

| Compound No.[2] | Example No. | R[1] | R[2] | R[3] | R[4] | R[5] |
|---|---|---|---|---|---|---|
| 1 | 19 | H | H | H | $CH_3$ | H |
| 2 | 23 | H | H | H | $C_2H_5$ | $CH_3$ |
| 3* | 26 | H | H | H | $CH_3$ | p-Cl-$C_6H_4$ |
| 4 | 1, 30 | 4-Cl | H | H | $CH_3$ | H |
| 5 | 8, 28, 33 | 4-F | H | H | $CH_3$ | H |
| 6 | 20 | 2-F | H | H | $CH_3$ | H |
| 7* | 9 | 4-Cl | H | H | $CH_3$ | $CH_3$ |
| 8* | 6 | 4-Br | H | H | $CH_3$ | $CH_3$ |
| 9* | 5, 31, 34 | 4-F | H | H | $CH_3$ | $CH_3$ |
| 10* | 20' | 4-Cl | H | H | $CH_3$ | n-Pr |
| 11* | 21 | 4-Cl | H | H | $CH_3$ | n-$C_5H_{11}$ |
| 12 | 27 | 4-Cl | H | H | $C_2H_5$ | $CH_3$ |
| 13 | 14 | 4-Cl | H | H | $-(CH_2)_4-$ | |
| 14 | 22 | 3-Cl | 4-Cl | H | $CH_3$ | H |
| 15 | 17, 32 | 3-Cl | 5-Cl | H | $CH_3$ | H |
| 16 | 7, 11, 15 | 2-Cl | 4-Cl | H | $CH_3$ | H |
| 17* | 13, 18 | 2-Cl | 4-Cl | H | $C_2H_5$ | $CH_3$ |
| 18 | 37 | 3-Cl | 5-Cl | H | $C_2H_5$ | $CH_3$ |
| 19 | 36 | 3-Cl | 5-Cl | H | $-(CH_2)_3-$ | |
| 20* | 24 | 3-Cl | 4-Cl | H | $C_6H_5$ | H |
| 21* | 25 | 3-Cl | 4-Cl | H | p-Cl-$C_6H_4$ | H |
| 22* | 29 | 3-Cl | 5-Cl | H | p-Cl-$C_6H_4$ | H |
| 23* | 4 | 2-F | 4-F | H | $CH_3$ | H |
| 24 | 12 | 2-Cl | 4-Cl | 6-Cl | $CH_3$ | H |
| 25 | 35 | 4-$CH_2CH_3$ | H | H | $CH_3$ | H |
| 26 | 2 | 2-Cl | 4-Cl | 5-iPrO | $CH_3$ | H |
| 27 | 3, 16 | 2-F | 4-Cl | 5-iPrO | $CH_3$ | H |
| 28 | 10 | 2-$NO_2$ | 4-$CF_3$ | H | $CH_3$ | H |
| 29 | 38 | 2-Cl | 5-$CF_3$ | H | $CH_3$ | n-Pr |
| 30 | | 2-Cl | 4-Cl | 5-HC≡$CCH_2O$ | $CH_3$ | H |
| 31* | | 2-Cl | 4-Cl | 5-HC≡$CCH_2O$ | $CH_3$ | $CH_3$ |
| 32 | 39, 45 | 2-F | 4-Cl | 5-HC≡$CCH_2O$ | $CH_3$ | H |
| 33* | | 2-F | 4-Cl | 5-HC≡$CCH_2O$ | $CH_3$ | $CH_3$ |
| 34 | | 2-F | 4-Br | 5-HC≡$CCH_2O$ | $CH_3$ | H |
| 35* | 40 | 2-F | 4-Br | 5-HC≡$CCH_2O$ | $CH_3$ | $CH_3$ |
| 36 | 41 | 2-F | 4-Cl | 5-HC≡$CC(CH_3)H_2O$ | $CH_3$ | H |
| 37 | | 2-F | 4-Cl | 5-$H_3$CC≡$CCH_2CH_2O$ | $CH_3$ | H |
| 38 | | 2-Cl | 4-Cl | 5-$H_3$CC≡$CCH_2CH_2O$ | $CH_3$ | H |
| 39 | | 2-F | 4-Cl | 5-$H_2C$=$CHCH_2O$ | $CH_3$ | H |
| 40* | | 2-F | 4-Br | 5-$H_2C$=$CHCH_2O$ | $CH_3$ | $CH_3$ |
| 41 | | 2-F | 4-Cl | 5-$H_2C$=$C(CH_3)CH_2O$ | $CH_3$ | H |
| 42 | | 2-Cl | 4-Cl | 5-$H_2C$=$C(CH_3)CH_2O$ | $CH_3$ | H |
| 43* | | 2-F | 4-Br | 5-HC(Cl)=$CHCH_2O$ | $CH_3$ | $CH_3$ |
| 44 | 44 | 2-F | 4-Cl | 5-$H_2C$=$C(Cl)CH_2O$ | $CH_3$ | H |
| 45 | | 2-F | 4-Cl | 5-$H_3$CCH=$C(Br)CH_2O$ | $CH_3$ | H |
| 46 | | 2-F | 4-Cl | 5-$CH_3CH_2OC(O)C(CH_3)HO$ | $CH_3$ | H |
| 47 | | 2-F | 4-Cl | 5-$CH_3CH_2OC(O)C(CH_3)HO$ | $CH_3$ | $CH_3$ |
| 48 | | 2-Cl | 4-Cl | 5-$CH_3CH_2OC(O)C(CH_3)HO$ | $CH_3$ | H |

TABLE 1-continued

Oxazolidinedione Derivatives[1]

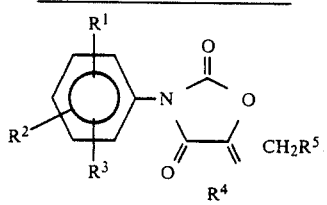

| Compound No.[2] | Example No. | R[1] | R[2] | R[3] | R[4] | R[5] |
|---|---|---|---|---|---|---|
| 49* | 42 | 2-Cl | 4-Cl | 5-CH$_3$CH$_2$OC(O)CHO(CH$_3$) | CH$_3$ | CH$_3$ |
| 50 |  | 2-Cl | 4-Cl | 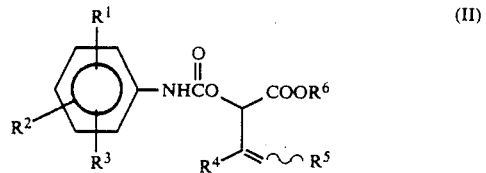 | CH$_3$ | H |
| 51* |  | 2-Cl | 4-Cl | 5-CH$_3$O | CH$_3$ | CH$_3$ |
| 52 | 46 | 2-F | 4-Cl | 5-CH$_3$O | CH$_3$ | H |
| 53* |  | 2-F | 4-Cl | 5-(CH$_3$)$_2$CHO | CH$_3$ | CH$_3$ |
| 54* |  | 2-F | 4-Br | 5-(CH$_3$)$_2$CHO | CH$_3$ | CH$_3$ |
| 55 |  | 2-F | 4-Cl | 5-cyclo-C$_5$H$_9$O | CH$_3$ | H |
| 56 |  | 2-F | 4-Cl | 5-cyclo-C$_6$H$_{11}$O | CH$_3$ | H |

[1]The abbreviations in the table are as follows:
n-Pr: n-propyl
C$_6$H$_5$: phenyl
i-PrO: isopropoxyl
n-C$_5$H$_{11}$: n-pentyl
p-Cl-C$_6$H$_4$: p-chlorophenyl
[2]The compounds asterisked are mixtures of cia and trans isomers with respect to the stereochemistry of the double bonds at the 5-positions of the oxazolidinedione rings.

New oxazolidinedione derivatives of the present invention, when used in paddy fields, exhibit a powerful weed-killing effect on annual weeds such as Deccan grasses (*Echinochloa Crus-galli* var.), *Monochoria vaginalis* var. and *Ammannia multiflora* Roxb. and perennial weeds such as *Cyperrus serotinus* Rottb., *Scirpus juncoides* subsp., *Sagittaria pygmaea* Miq. and *Eleocharis acicularis* Romer et Schultes. In plowed fields, the derivatives can selectively kill weeds such as *Amaranthus lividus* L., *Digitaria sanguinalis* Scopoli, *Setaria viridis* P. Beauv., *Chenopodium album* L., *Polygonum caespitosum* var., *Amaranthus patulus* Bertoloni., *Portulaca oleracea* L. and *Plantago asiatica* L.

The compounds of the present invention have a vigorous weed-killing activity and can achieve the expected effect in small amounts, though producing only extremely small phytotoxicity for useful cultured plants. In other words, the compounds of the present invention kill weeds belonging to grass species such as Deccan grasses, *Digitaria sanguinalis* Scopoli and *Setaria viridis* P. Beauv., while they produce almost no phytotoxicity for crops belonging to such species as transplanted paddy rice, wheat and corn. No phytotoxicity is observed for groups belonging to species other than grasses, such as soybeans and cotton.

The compounds of the present invention are mixed with various carriers, fillers, solvents, surfactants and stabilizers and prepared by a conventional method when used as herbicides in any desired form, for example, water-dispersible powders, emulsions, powders, or granules.

In addition, the compounds can be mixed with other active ingredients such as other herbicides, insecticides, fungicides or growth modifiers during the preparation process.

Herbicides containing the compounds of the present invention are applied in such a manner that they contain 10 to 500 g of the compounds, preferably 30 to 300 g, relative to 10 ares, depending upon the methods employed, seasons, and the kinds of plant concerned.

New oxazolidinedione derivatives expressed by the formula (I) of the present invention can be easily obtained by treating carbamates expressed by the following formula (II):

$$\text{(II)}$$

[wherein R$^1$, R$^2$, R$^3$, R$^4$ and R$^5$ denote the same as those described above and R$^6$ denotes a lower alkyl group (C$_1$ to C$_4$)] with a base. The reaction is preferably effected in an ordinary organic solvent under heating or reflux.

The treatment of the carbamates expressed by the formula (II) with a base is essential matter for the above-described first method of the present invention. Examples of the base used include tertiary amines such as triethylamine, tripropylamine, tributylamine, N-methylmorpholine, and dimethylaniline, aromatic amines such as pyridine, lutidine, and pyrimidine, alkali metal alkoxides such as sodium methoxide, sodium ethoxide, and potassium t-butoxide, alkali metal hydrides such as sodium hydride and potassium hydride, and basic inorganic compounds such as sodium carbonate, potassium carbonate, sodium hydroxide, and potassium hydroxide. A sufficient amount of the base used is a catalytic amount.

The compounds expressed by the formula (II) which are materials of the present invention can be easily produced in accordance with the following method.

Aryl isocyanates or carbamoyl chlorides expressed by the following formula (III):

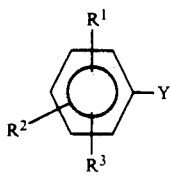
(III)

(wherein $R^1$, $R^2$ and $R^3$ denote the same as those described above and Y denotes an isocyanato or carbamoyl chloride group) is reacted with $\beta,\gamma$-unsaturated-$\alpha$-hydroxycarboxylic acid esters expressed by the following formula (IV):

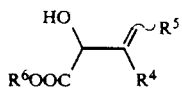
(IV)

(wherein $R^4$, $R^5$ and $R^6$ denote the same as those described above).

The aryl isocyanates and carbamoyl chlorides expressed by the formula (III) are compounds which can be easily obtained, for example, from the corresponding aniline derivatives. Examples of the aryl isocyanates include phenyl isocyanate and substituted phenyl isocyanates such as o, m or p-fluorophenyl isocyanate, o, m or p-chlorophenyl isocyanate, o, m or p-bromophenyl isocyanate, o, m, or p-iodophenyl isocyanate, 2,3-dichlorophenyl isocyanate, 2,4-dichlorophenyl isocyanate, 2,5-dichlorophenyl isocyanate, 3,4-dichlorophenyl isocyanate, 3,5-dichlorophenyl isocyanate, 2,3-difluorophenyl isocyanate, 2,4-difluorophenyl isocyanate, 2,5-difluorophenyl isocyanate, 3,4-difluorophenyl isocyanate, 3,5-difluorophenyl isocyanate, 2,4-dibromophenyl isocyanate, 2,4,6-trichlorophenyl isocyanate, 2,4,5-trichlorophenyl isocyanate, 3,4,5-trichlorophenyl isocyanate, 2,4,6-trifluorophenyl isocyanate, 2-chloro-4-fluorophenyl isocyanate, 2-fluoro-4-chlorophenyl isocyanate, 2-chloro-4-bromophenyl isocyanate, 2-fluoro-4-bromophenyl isocyanate, 2-chloro-4-iodophenyl isocyanate, 2,4-dichloro-6-fluorophenyl isocyanate, 3,5-dichloro-4-fluorophenyl isocyanate, 3,5-dichloro-4-bromophenyl isocyanate, 3,4-dichloro-5-fluorophenyl isocyanate, 2,4-dichloro-6-bromophenyl isocyanate, 2,4-dichloro-5-fluorophenyl isocyanate, 2,4-difluoro-6-chlorophenyl isocyanate, o, m or p-methylphenyl isocyanate, o, m or p-ethylphenyl isocyanate, o, m or p-isopropylphenyl isocyanate, o, m or p-t-butylphenyl isocyanate, 2-chloro-5-methylphenyl isocyanate, 2-fluoro-5-methylphenyl isocyanate, 4-chloro-5-methylphenyl isocyanate, 2-chloro-4-isopropylphenyl isocyanate, 2,4-dichloro-5-methylphenyl isocyanate, 2,4-difluoro-5-methylphenyl isocyanate, 2-fluoro-4-chloro-5-methylphenyl isocyanate, o, m or p-methoxyphenyl isocyanate, o, m or p-isopropoxyphenyl isocyanate, o, m or p-t-butoxyphenyl isocyanate, 2-chloro-5-methoxyphenyl isocyanate, 2-fluoro-5-methoxyphenyl isocyanate, 4-chloro-5-methoxyphenyl isocyanate, 2,4-dichloro-5-isopropoxyphenyl isocyanate, 2,4-difluoro-5-isopropoxyphenyl isocyanate, 2-fluoro-4-chloro-5-isopropoxyphenyl isocyanate, 2,4-dichloro-5-methoxyphenyl isocyanate, 2,4-dichloro-5-ethoxyphenyl isocyanate, -fluoro-4-chloro-5-methoxyphenyl isocyanate, 2-fluoro-4-chloro-5-ethoxyphenyl isocyanate, 2-fluoro-4-bromo-5-isopropoxyphenyl isocyanate, 2,4-dichloro-5-t-butoxyphenyl isocyanate, o, m or p-nitrophenyl isocyanate, 2-chloro-4-nitrophenyl isocyanate, 2-fluoro-4-nitrophenyl isocyanate, 2-nitro-4-chlorophenyl isocyanate, 2-nitro-4-fluorophenyl isocyanate, o, m or p-trifluoromethylphenyl isocyanate, o, m or p-(fluoromethyl)phenyl isocyanate, o, m or p-(chloromethyl)phenyl isocyanate, o, m or p-(bromomethyl)phenyl isocyanate, 2-chloro-5-trifluoromethylphenyl isocyanate, 2-fluoro-5-trifluoromethylphenyl isocyanate, 4-chloro-5-trifluoromethylphenyl isocyanate, 2-nitro-4-trifluoromethylphenyl isocyanate, 2-trifluoromethyl-4-nitrophenyl isocyanate, 3,5-dichloro-4-nitrophenyl isocyanate, 2-nitro-5-methylphenyl isocyanate, 3-nitro-4-methylphenyl isocyanate, 2-trifluoromethyl-4-bromophenyl isocyanate, and 3,5-bis(trifluoromethyl)phenyl isocyanate. Examples of the carbamoyl chloride derivatives include phenylcarbamoyl chloride and substituted phenylcarbamoyl chlorides such as o, m or p-fluorophenylcarbamoyl chloride, o, m or p-bromophenylcarbamoyl chloride, o, m or p-chlorophenylcarbamoyl chloride, o, m or p-iodophenylcarbamoyl chloride, 2,3-dichlorophenylcarbamoyl chloride, 2,4-dichlorophenylcarbamoyl chloride, 2,5-dichlorophenylcarbamoyl chloride, 3,4-dichlorophenylcarbamoyl chloride, 3,5-dichlorophenylcarbamoyl chloride, 2,3-difluorophenylcarbamoyl chloride, 2,4-difluorophenylcarbamoyl chloride, 3,5-difluorophenylcarbamoyl chloride, 2,4-dibromophenylcarbamoyl chloride, 2,4,6-trichlorophenylcarbamoyl chloride, 2,4,5-trichlorophenylcarbamoyl chloride, 2-chloro-4-fluorophenylcarbamoyl chloride, 2-fluoro-4-chlorophenylcarbamoyl chloride, 2-chloro-4-bromophenylcarbamoyl chloride, 2-chloro-4-iodophenylcarbamoyl chloride, 3,5-dichloro-4-fluorophenylcarbamoyl chloride, 3,5-dichloro-4-bromophenylcarbamoyl chloride, 2,4-dichloro-6-fluorophenylcarbamoyl chloride, o, m or p-methylphenylcarbamoyl chloride, o, m or p-isopropylphenylcarbamoyl chloride, 2-chloro-5-methylphenylcarbamoyl chloride, 2-fluoro-5-methylphenylcarbamoyl chloride, 4-chloro-5-methylphenylcarbamoyl chloride, 2-fluoro-4-isopropylphenylcarbamoyl chloride, 2,4-dichloro-5-methylphenylcarbamoyl chloride, o, m or p-methoxyphenylcarbamoyl chloride, o, m or p-ethoxyphenylcarbamoyl chloride, o, m or p-t-butoxyphenylcarbamoyl chloride, 2-chloro-5-methoxyphenylcarbamoyl chloride, 2-fluoro-5-methoxyphenylcarbamoyl chloride, 4-chloro-5-methoxyphenylcarbamoyl chloride, 2,4-dichloro-5-isopropoxyphenylcarbamoyl chloride, 2,4-dichloro-5-methoxyphenylcarbamoyl chloride, 2,4-dichloro-5-ethoxyphenylcarbamoyl chloride, 2,4-difluoro-5-methoxyphenylcarbamoyl chloride, 2,4-difluoro-ethoxyphenylcarbamoyl chloride, 2,4-difluoro-5-isopropoxyphenylcarbamoyl chloride, 2-fluoro-4-chloro-5-methoxyphenylcarbamoyl chloride, 2-fluoro-4-chloro-5-ethoxyphenylcarbamoyl chloride, 2-fluoro-4-chloro-5-isopropoxyphenylcarbamoyl chloride, 2-fluoro-4-chloro-5-t-butoxyphenylcarbamoyl chloride, 2-chloro-4-fluoro-5-methoxyphenylcarbamoyl chloride, 2-fluoro-4-bromo-5-isopropoxyphenylcarbamoyl chloride, o, m or p-nitrophenylcarbamoyl chloride, 2-chloro-4-nitrophenylcarbamoyl chloride, 2-fluoro-4-nitrophenylcarbamoyl chloride, 2-nitro-4-fluorophenylcarbamoyl chloride, 2-bromo-4-nitrophenylcarbamoyl chloride, o, m or p-trifluoromethylphenylcarbamoyl chloride, o, m or p-(fluoromethyl)phenylcarbamoyl chloride, o, m or p-(chloromethyl)phenylcarbamoyl chloride, o, m or p-(bromomethyl)phenylcarbamoyl chloride, 2-chloro-5-trifluoromethylphenylcarbamoyl chloride, 2-fluoro-5-trifluoromethylphenylcarbamoyl chloride, 4-chloro-5-trifluoromethylphenylcarbamoyl chloride, 2-nitro-4-trifluoromethylphenylcarbamoyl chloride, 2-trifluoromethyl-4-nitrophenylcarbamoyl chloride, 2-nitro-4-trifluoromethyl-5-methoxyphenylcarbamoyl chloride, 3,5-dichloro-4-nitrophenylcarbamoyl chloride, 2-nitro-5-methylphenylcarbamoyl chloride, 2-trifluoromethyl-4-bromophenylcarbamoyl chloride, and 3,5-bis(trifluoromethyl)phenylcarbamoyl chloride. The 2-hydroxycarboxylic acid esters expressed by the formula (IV) can be easily produced from inexpensive materials available at the market. Examples of the esters include methyl 2-hydroxy-3-methyl-3-butenoate, methyl 2-hydroxy-3-methyl-3-pentenoate, methyl 2-hydroxy-3-ethyl-3-butenoate, methyl 2-hydroxy-3-ethyl-3-pentenoate, methyl 2-hydroxy-3-butyl-3-butenoate, methyl 2-hydroxy-3-methyl-3-heptenoate, methyl 2-hydroxy-3-methyl-3-nonenoate, methyl 2-hydroxy-3-hexyl-3-butenoate, methyl 2-hydroxy-3-(1'-cyclopentenyl) acetate, methyl 2-hydroxy-3-(1'-cyclohexenyl) acetate, methyl 2-hydroxy-3-(1'-cycloheptenyl) acetate, methyl -hydroxy-3-butyl-3-pentenoate, methyl 2-hydroxy-3-(1'-cyclododecenyl) acetate, methyl 2-hydroxy-3-ethyl-3-heptenoate, methyl 2-hydroxy-3-penthyl-3-octenoate, methyl -hydroxy-3-phenyl-3-butenoate, methyl 2-hydroxy-3-phenyl-3-pentenoate, methyl 2-hydroxy-3-phenyl-3-hexenoate, methyl 2-hydroxy-3-(4'-chlorophenyl)-3-butenoate, methyl 2-hydroxy-3-(4'-bromophenyl)- 3-butenoate, methyl 2-hydroxy-3-(3',4'-dimethoxyphenyl)-3-butenoate, methyl 2-hydroxy-3-(3',4'-dichlorophenyl)-3-butenoate, methyl 2-hydroxy-3-(4'-methylphenyl)-3-butenoate, methyl 2-hydroxy-3-(4'-chlorophenyl)-3-pentenoate, methyl 2-hydroxy-3-(4'-fluorophenyl)-3-pentenoate, and methyl 2-hydroxy-3-(3',5'-dichlorophenyl)-3-butenoate, and lower alkyl esters thereof such as ethyl esters, isopropyl esters, isobutyl esters, and t-butyl esters. The reactions between the compounds expressed by the formula (III) and the compounds expressed by the formula (IV) are effected in an organic solvent, in the presence of a base in some cases, at room temperature or reflux temperature to produce the compounds expressed by the formula (II) (refer to Examples 1 to 3 described below).

Examples of the carbamates expressed by the formula (II) include methyl 2-(N-phenylcarbamoyloxy)-3-methyl-3-butenoate, ethyl 2-(N-phenylcarbamoyloxy)-3-methyl-3-butenoate, isobutyl 2-(N-phenylcarbamoyloxy)-3-methyl-(3-butenoate, methyl 2-{N-(2'-chlorophenyl)carbamoyloxy}-3-methyl-3-butenoate, methyl 2-{N-(2'-fluorophenyl)carbamoyloxy}-3-methyl-3-butenoate, methyl 2-{N-(3'-fluorophenyl)carbamoyloxy]-3-methyl-3-butenoate, methyl 2-{N-(2'-bromophenyl)carbamoyloxy}-3-methyl-3-butenoate, methyl 2-{N-(4'-chlorophenyl)carbamoyloxy]-3-methyl-3-butenoate, methyl 2-{N-(4'-fluorophenyl)carbamoyloxy}-3-methyl-3-butenoate, methyl 2-{N-(4'-bromophenyl)carbamoyloxy]-3-methyl-3-butenoate, methyl 2-{N-(2',4'-dichlorophenyl)carbamoyloxy}-3-methyl-3-butenoate, methyl 2-{N-(2',5'-dichlorophenyl)carbamoyloxy}-3-methyl-3-butenoate, methyl 2-{N-(3',4'-dichlorophenyl)carbamoyloxy}-3-methyl-3-butenoate, methyl 2-{N-(3',5'-dichlorophenyl)carbamoyloxy}-3-methyl-3-butenoate, methyl 2-{N-(2',4'-difluorophenyl)carbamoyloxy}-3-methyl-3-butenoate, methyl 2-{N-(2',4'-dibromophenyl)carbamoyloxy}-3-methyl-3-butenoate, methyl 2-{N-(2'-chloro-4'-fluorophenyl)carbamoyloxy}-3-methyl-3-butenoate, methyl 2-{N-(2'-bromo-4'fluorophenyl)carbamoyloxy}-3-methyl-3-butenoate, methyl 2-{N-(2'-bromo-4'-chlorophenyl)carbamoyloxy}-3-methyl-3-butenoate, methyl 2-{N-(2',4',6'-trichlorophenyl)carbamoyloxy}-3-methyl-3-butenoate, methyl 2-{N-(2',4',6'-trifluorophenyl)carbamoyloxy}-3-methyl-3-butenoate, methyl 2-{N-(2',4',6'-tribromophenyl)carbamoyloxy}-3-methyl-3-butenoate, methyl 2-{N-(3',5'-dichloro-4'-fluorophenyl)carbamoyloxy}-3-methyl-3-butenoate, methyl 2-{N-(3'-chloro-4'-methylphenyl)carbamoyloxy}-3-methyl-3-butenoate, methyl 2-{N-(3'-fluoro-4'-methylphenyl)carbamoyloxy}-3-methyl-3-butenoate, methyl 2-{N-(4'-methylphenyl)carbamoyloxy}-3-methyl-3-butenoate, methyl 2-{N-(4'-ethylphenyl)carbamoyloxy}-3-methyl-3-butenoate, methyl 2-{N-(2'-trifluoromethylphenyl)carbamoyloxy}-3-methyl-3-butenoate, methyl 2-{N-(3'trifluoromethylphenyl)carbamoyloxy}-3-methyl-3-butenoate, methyl 2-{N-(4'-trifluoromethylphenyl)carbamoyloxy}-3-methyl-3-butenoate, methyl 2-[N-{3',5'-bis(trifluoromethyl)phenyl}carbamoyloxy]-3-methyl-3-butenoate, methyl 2-{N-(2'-chloromethylphenyl)carbamoyloxy}-3-methyl-3-butenoate, methyl 2-{N-(4'-bromomethylphenyl)carbamoyloxy}-3-methyl-3-butenoate, methyl 2-{N-(2'-nitrophenyl)carbamoyloxy}-3-methyl-3-butenoate, methyl 2-{N-(3'-nitrophenyl)carbamoyloxy}-3-methyl-3-butenoate, methyl 2-{N-(4'-nitrophenyl)carbamoyloxy}-3-methyl-3-butenoate, methyl 2-{N-(2',4'-dinitrophenyl)carbamoyloxy}-3-methyl-3-butenoate, methyl 2-{N-(3',5'-dinitrophenyl)carbamoyloxy}-3-methyl-3-butenoate, methyl 2-{N-(2'-methoxyphenyl)carbamoyloxy}-3-methyl-3-butenoate, methyl 2-{N-(4'-methoxyphenyl)carbamoyloxy}-3-methyl-3-butenoate, methyl 2-{N-(2'-chloro-5'-trifluoromethylphenyl)carbamoyloxy}-3-methyl-3-butenoate, methyl 2-{N-(2'-trifluoromethyl-4'-bromophenyl)carbamoyloxy}-3-methyl-3-butenoate, methyl 2-{N-(3'-trifluoromethyl-4'-fluorophenyl)carbamoyloxy}-3-methyl-3-butenoate, methyl 2-{N-(2'-chloro-4'-nitrophenyl)carbamoyloxy}-3-methyl-3-butenoate, methyl 2-{N-(2'-chloro-5'-methoxyphenyl)carbamoyloxy}-3-methyl-3-butenoate, methyl 2-{N-(3'-nitro-4'-methylphenyl}carbamoyloxy)-3-methyl-3-butenoate, methyl 2-{N-(4'-nitro-2'-trifluoromethylphenyl)carbamoyloxy}-3-methyl-3-butenoate, methyl 2-{N-(2'-nitro-4'-trifluoromethylphenyl)carbamoyloxy}-3-methyl-3-butenoate, trifluoromethylphenyl)carbamoyloxy}-3-methyl-3-butenoate, methyl 2-{N-(3'-methoxy-5'-trifluoromethylphenyl)carbamoyloxy}-3-methyl-3-butenoate, methyl 2-{N-(2'-methoxy-5'-nitrophenyl)carbamoyloxy}-3-methyl-3-butenoate, methyl 2-{N-(2',4'-dichloro-5'-methoxyphenyl)carbamoyloxy}-3-methyl-3-butenoate, methyl 2-{N-(4'-chloro-2'-fluoro-5'-methoxyphenyl)carbamoyloxy}-3-methyl-3-butenoate, methyl 2-{N-(4'-bromo-2'-fluoro-5'-ethoxyphenyl)carbamoyloxy}-3-methyl-3-butenoate, methyl 2-{N-(2',4'-dichloro-5'-methoxyphenyl)carbamoyloxy}-3-methyl-3-butenoate, ethyl 2-{N-(2',4'-dichloro-5'-ethoxyphenyl)carbamoyloxy}-3-methyl-3-butenoate, isobutyl 2-{N-(2',4'-dichloro-5'-isopropoxyphenyl)carbamoyloxy}-3-methyl-3-butenoate, methyl 2-{N-(2',4'-dichloro-5'-t-butoxyphenyl)carbamoyloxy}-3-methyl-3-butenoate, isobutyl 2-{N-(2',4'-dichloro-5'-hexyloxyphenyl)carbamoyloxy}-3-methyl-3-butenoate, methyl 2-{N-(4'-chloro-2'-fluoro-5'-methoxyphenyl)carbamoyloxy}-3-methyl-3-butenoate, ethyl 2-{N-(4'-chloro-2'-fluoro-5'-ethoxyphenyl)carbamoyloxy}-3-methyl-3-butenoate, methyl 2-{N-(4'-chloro-2'-fluoro-5'isopropoxyphenyl)carbamoyloxy}-3-methyl-3-butenoate, isobutyl 2-{N-(4'-chloro-2'-fluoro-5'-isopropoxyphenyl)carbamoyloxy}-3-methyl-3-butenoate, methyl 2-{N-(4'-chloro-2'-fluoro-5'-t-butoxyphenyl)carbamoyloxy}-3-methyl-3-butenoate, methyl 2-{N-(4'-chloro-2'-fluoro-5'-isobutoxyphenyl)carbamoyloxy}-3-methyl-3-pentenoate, isobutyl 2-{N-(4'-chloro-2'-fluoro-5'-methoxyphenyl)carbamoyloxy}-3-methyl-3-pentenoate, methyl 2-{N-(4'-chloro-2'-fluoro-5'-ethoxyphenyl)carbamoyloxy}-3-methyl-3-pentenoate, methyl 2-{N-(4'-chloro-2'-fluoro-5'-isopropoxyphenyl)carbamoyloxy}-3-methyl-3-pentenoate, isobutyl 2-{N-(4'-chloro-2'-fluoro-5'-isopropoxyphenyl)carbamoyloxy}-3-octyl-3-pentenoate, methyl 2-{N-(4'-chloro-2'-fluoro-5'-t-butoxyphenyl)carbamoyloxy}-3-methyl-3-pentenoate, methyl 2-{N-(4'-chloro-2'-fluoro-5'-isopropoxyphenyl)carbamoyloxy}-3methyl-3-pentenoate, isobutyl 2-{N-(4'-chloro-2'-fluoro-5'-isopropoxyphenyl)carbamoyloxy}-3-octhyl-3-pentenoate, methyl 2-{N-(4'-chloro-2'-fluoro-5'-t-butoxyphenyl)carbamoyloxy}-3-methyl-3-pentenoate, methyl 2-{N-(4'-chloro-2'-fluoro-5-methoxyphenyl)carbamoyloxy}-3-ethyl-3-butenoate, isobutyl 2-{N-(4-chloro-2-'-fluoro-5-'hexyloxyphenyl)carbamoyloxy}-3-ethyl-3-butenoate, methyl 2-{N-(4'-chloro-2'-fluoro-5'-ethoxyphenyl)carbamoyloxy}-3-ethyl-3-butenoate, methyl 2-{N-(4'-chloro-3'-isopropoxyphenyl)carbamoyloxy}-3-methyl-3-butenoate, isobutyl 2-{N-(4'-chloro-2'-fluoro-5'-isopropoxyphenyl)carbamoyloxy}-3-octyl-3-butenoate, methyl 2-{N-(4'-chloro-2'-fluoro-5'-t-butoxyphenyl)carbamoyloxy}-3-ethyl-3-butenoate, methyl 2-{N-(4'-chloro-3'-methoxyphenyl)carbamoyloxy}-3-methyl-3-butenoate, isobutyl 2-{N-(4'-chloro-3'-methoxyphenyl)carbamoyloxy}-3-methyl-3-butenoate, ethyl 2-{N-(4'-chloro-3'-ethoxyphenyl)carbamoyloxy}-3-methyl-3-butenoate, methyl 2-{N-(4'-chloro-3'-isopropoxyphenyl)carbamoyloxy}-3-methyl-3-butenoate, isobutyl 2-{N-(4'-chloro-3'-isopropoxyphenyl)carbamoyloxy}-3-methyl-3-butenoate, isobutyl 2-{N-(4'-chloro-3'-pentyloxyphenyl)carbamoyloxy}-3-methyl-3-butenoate, isobutyl 2-{N-(4'-chloro-3'-hexyloxyphenyl)carbamoyloxy}-3-methyl-3-butenoate, isobutyl 2-{N-(4'-chloro-3'-heptylixyphenyl)carbamoyloxy}-3-methyl-3-butenoate, isobutyl 2-{N-(4'-chloro-3'-octyloxyphenyl)carbamoyloxy)-3-methyl-3-butenoate, isobutyl 2-{N-(4'-chloro-3'-nonyloxyphenyl)carbamoyloxy}-3-methyl-3-butenoate, methyl 2-{N-(4'-fluoro-3'-methoxyphenyl)carbamoyloxy}-3-methyl-3-butenoate, isobutyl 2-{N-(4'-fluoro-3'-isopropoxyphenyl)carbamoyloxy}-3-methyl-3-butenoate, ethyl 2-{N-(4'-fluoro-3'-octyloxyphenyl)carbamoyloxy}-3-methyl-3-butenoate, methyl 2-{N-(4'-chloro-3'-isopropoxyphenyl)carbamoyloxy}-3-methyl-3-pentenoate, methyl 2-{N-(4'-chloro-3'-isopropoxyphenyl)carbamoyloxy}-3-methyl-3-hexenoate, methyl 2-{N-(4'-fluoro-3'-isopropoxyphenyl)carbamoyloxy}-3-methyl-3-heptenoate, methyl 2-{N-(4'-chloro-3'-isopropoxyphenyl)carbamoyloxy}-3-methyl-3-octenoate, methyl 2-{N-(4'-chloro-3'-isopropoxyphenyl)carbamoyloxy}-3-octyl-3-butenoate, isobutyl 2-{N-(4'-chloro-3'-isopropoxyphenyl)carbamoyloxy}-3-octyl-3-octenoate, methyl 2-{N-(4'-fluoro-3'-isopropoxyphenyl)carbamoyloxy}-3-methyl-3-pentenoate, isobutyl 2-{N-(4'-fluoro-3'-isopropoxyphenyl)carbamoyloxy}-3-dodecyl-3-pentenoate, methyl 2-{N-(4'-fluorophenyl)carbamoyloxy}-3-methyl-3-pentenoate, methyl 2-{N-(4'-fluorophenyl)carbamoyloxy}-3-ethyl-3-butenoate, isobutyl 2-{N-(4'-chlorophenyl)carbamoyloxy}-3-ethyl-3-butenoate, methyl 2-{N-(4'-chlorophenyl)carbamoyloxy}-3-methyl-3-pentenoate, methyl 2-{N-(4'-bromophenyl)carbamoyloxy}-3-ethyl-3-butenoate, methyl 2-{N-(4'-bromophenyl)carbamoyloxy}-3-methyl-3-pentenoate, methyl 2-{N-(2',4'-dichlorophenyl)carbamoyloxy}-3-ethyl-3-pentenoate, methyl 2{N-(4'chlorophenyl)carbamoyloxy}-2-(1''-cyclohexenyl) acetate, methyl 2-{N-(4'-chlorophenyl)carbamoyloxy}-3-methyl-3-heptenoate, methyl 2-{N-(4'-chlorophenyl)carbamoyloxy}-3-butyl-3-butenoate, methyl 2-{N-(4'-chlorophenyl)carbamoyloxy}-3-methyl-3-nonenoate, methyl 2-{N-(4'-chlorophenyl)carbamoyloxy}-3-hexyl-3-butenoate, methyl 2-(N-phenylcarbamoyloxy)-3-ethyl-3-pentenoate, methyl 2-{N-(3',4'-dichlorophenyl)carbamoyloxy}-3-phenyl-3-butenoate, methyl 2-{N-(3',4'-dichlorophenyl)carbamoyloxy]-3-(4''-chlorophenyl)-3-butenoate, methyl 2-{N-(3',5'-dichlorophenyl)carbamoyloxy}-3-(4''-fluorophenyl)-3-butenoate, methyl 2-{N-(3',5'-dichlorophenyl)carbamoyloxy}-3-(4''-fluorophenyl)-3-butenoate, methyl 2-{N-(2'-fluoro-4'-chloro-5'-isopropoxyphenyl)carbamoyloxy}-3-(4''-fluorophenyl)-3-butenoate, methyl 2-{N-phenylcarbamoyloxy)-3-(4'-chlorophenyl)-3-butenoate, methyl 2-{N-(4'-chlorophenyl)carbamoyloxy}-3-ethyl-3-pentenoate, methyl 2-{N-(4'-fluorophenyl)carbamoyloxy}-3-methyl-3-pentenoate, methyl 2-{N-(4'-fluorophenyl)carbamoyloxy}-3-ethyl-3-butenoate, methyl 2-{N-(3',5'-dichlorophenyl)carbamoyloxy}-2-(1''-cyclopentenyl) acetate, methyl 2-{N-(2'-fluoro-4'-chloro-5'-isopropoxyphenyl)carbamoyloxy}-2-(1''-cyclohexenyl) acetate, methyl 2-{N-(2',4'-dichloro-5'-isopropoxyphenyl)carbamoyloxy}-2-(1''-cyclododecenyl) acetate, methyl 2-{N-(2'-chloro-5'-trifluoromethylphenyl)carbamoyloxy}-3-methyl-3-pentenoate, methyl 2-{N-(2'-chloro-5'-trifluoromethylphenyl)carbamoyloxy}-3-butyl-3-butenoate, ethyl 2-{N-(2'-chloro-5'-trifluoromethylphenyl)carbamoyloxy}-3-methyl-3-pentenoate, isobutyl 2-{N-(2'-chloro-5'-trifluoromethylphenyl)carbamoyloxy}-3-methyl-3-pentenoate, isobutyl 2-{N-(2'-chloro-5'-trifluoromethylphenyl)carbamoyloxy}-3-butyl-3-butenoate, isopropoxyphenyl)carbamoyloxy}-3-butyl-3-butenoate, isobutyl 2-{N-(2'-fluoro-4'-isopropoxyphenyl)carbamoyloxy}-3-butyl-3-butenoate, methyl 2{N-(2'-fluoro-4'-chloro-5'-isopropoxyphenyl)carbamoyloxy}-3-methyl-3-pentenoate, isobutyl 2-{N-(2'-fluoro-4'-chloro-5'-isopropoxyphenyl)carbamoyloxy}-3-methyl-3-pentenoate, methyl 2-{N-(3',5'-dichlorophenyl)carbamoyloxy}-3-(4''-chlorobenzyl)-3-butenoate, ethyl 2-{N-(3',5'-dichlorophenyl)carbamoyloxy}-3-(4''-fluorobenzyl)-3-butenoate, isobutyl 2-{N-(3',5'-dichlorophenyl)carbamoyloxy}-3-(3'',5''-dichlorobenzyl)-3-butenoate, methyl 2-{N-(3',5'-dichlorophenyl)carbamoyloxy}-3-methyl-4-(4''-dichlorophenyl)-3-butenoate, ethyl 2-{N-(3',5'-dichlorophenyl)carbamoyloxy}-3-methyl-4-(4''-fluorophenyl)-3-butenoate, and isobutyl 2-{N-(3',5'-dichlorophenyl)-3-butenoate. These compounds can be used as the materials of the reaction of the present invention.

In the operation of the reaction of the present invention, the carbamates expressed by the formula (II) which are produced by the reaction between the compounds expressed by the formulae (III) and (IV) are treated with a base, without being isolated from the reaction system, to produce oxazolidinedione derivatives expressed by the formula (I) which is an object of the invention.

Examples of the organic solvents used in this reaction include aromatic solvents such as benzene, toluene, and xylene, ether solvents such as dioxane, tetrahydrofuran, and dimethoxyethane, alcohol solvents such as methanol, ethanol, and isobutyl alcohol, ethyl acetate, dimethylformamide, and dimethyl sulfoxide.

In the operation of the reaction of the present invention, the solvent can be removed from the reaction mixture after the reaction has been completed and the mixture can be subjected to separating purification using a silica gel column. However, pure oxazolidinedione derivatives can be easily isolated by adding a solvent such as an alcohol solvent in which the derivatives are not dissolved and filtering the crystals separated, if necessary, by cooling.

Of the compounds of the present invention expressed by the above-described formula (I), compounds expressed by the following formula (I'):

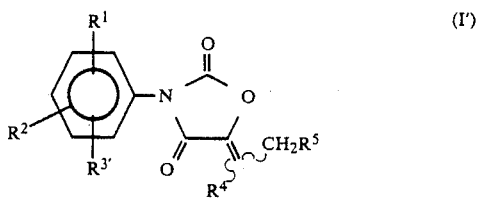

(I')

(wherein $R^1$, $R^2$, $R^4$ and $R^5$ denotes the same as those described above and $R^{3'}$ denotes —O—$R^7$ ($R^7$ denotes a substituted or non-substituted alkyl, alkenyl, alkynyl or cycloalkyl group having carbon atoms of the number which is the same as that of $R^3$ in the formula (I)) can be produced by a second method described below.

These compounds can be produced by the reaction between phenol derivatives expressed by the following formula (V):

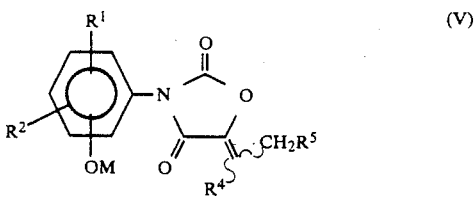

(V)

(wherein $R^1$, $R^2$, $R^4$ and $R^5$ denote the same as those described above and M denotes a hydrogen atom or an alkali metal) and compounds expressed by the following formula:

$$R^7-Y \quad (VI)$$

(wherein $R^7$ denotes a substituted or non-substituted alkyl, alkenyl, alkynyl or cycloalkyl group and Y denotes a group which is released) (when M in the formula (V) is a hydrogen atom, the reaction is effected in the presence of a base).

The reaction is preferably effected in an organic solvent. Examples of the organic solvent include aliphatic hydrocarbons such as hexane, heptane and ligroin, aromatic hydrocarbons such as benzene, toluene and xylene, ethers such as diethyl ether, diisopropyl ether, dioxane, tetrahydrofuran and ethylene glycol dimethyl ether, ketones such as acetone and methylethyl ketone, nitriles such as acetonitrile and isobutyronitrile, amides such as N,N-dimethylformamide, sulfur compounds such as dimethyl sulfoxide and sulfolan, and mixtures thereof.

Examples of the base used in the reaction between the compounds expressed by the formulae (V) and (VI) when M in the formula (V) is a hydrogen atom include organic bases such as pyridine, triethylamine and N,N-dimethylaniline, inorganic salt bases such as sodium hydroxide, potassium hydroxide, sodium carbonate and potassium carbonate, alkali metal alkoxides such as sodium methoxide and sodium ethoxide and carboxylic acid alkali metal salts such as sodium acetate and potassium acetate.

When chlorides, bromides or sulfonates are used as the compounds expressed by the formula (VI) in this reaction, the reaction can be caused to rapidly proceed by adding an iodide such as potassium iodide or sodium iodide or a quaternary ammonium salt such as tetraethylammonium bromide or benzyltriethyl ammonium bromide or iodide thereof, depending upon the compounds used, whereby the compounds of the present invention can be obtained in a good yield.

After the reaction has been completed, the products can be obtained by ordinary post-treatments but they can be purified by means of column chromatography or recrystallization, if required.

The compounds expressed by the formula (VI) which are the materials of the reaction can be easily obtained or prepared from materials available on the market. Examples of these compounds include alkyl halides such as methyl bromide, methyl iodide, ethyl bromide, ethyl iodide, isopropyl bromide, isopropyl iodide, butyl bromide, butyl iodide, sec-butyl bromide, cyclohexyl iodide, cyclohexyl bromide, cyclopentyl bromide, cyclopentyl iodide and cyclopropyl bromide, acethylene compounds such as propargyl chloride, propargyl bromide, propargyl iodide, 1-bromo-2-butyne, 1-chloro-2-butyne, 2-chloro-1-butyne, 2-bromo-1-butyne, 3-bromo-3-methyl-1-butyne, 3-chloro-3-methyl-1-butyne, 1-bromo-2-pentyne, 6-chloro-1-hexyne, 1-bromo-3-pentyne, 3-bromo-1-butyne, 3-chloro-1-butyne, and 4-bromo-1-butyne, olefin compounds such as allyl bromide, allyl chloride, methyllyl bromide, crotyl chloride, crotyl bromide, 1,3-dichloro-1-propene, 2,3-dichloro-1-propene, 4-bromo-3-methyl-1-butene, prenyl bromide, 3-bromo-3-methyl-1-butene and 2,3-dibromo-1-butene, substituted alkyl halogen compounds such as ethyl 2-bromoacetate, ethyl 2-chloroacetate, methyl 2-bromopropionate, ethyl 2-bromoacetate, isopropyl 2-bromoacetate and (2'-ethyl)hexyl 2-bromopropionate, 2-bromoacetate, ethyl 2-chloroacetate, methyl 2-bromopropionate, ethyl 2-bromoacetate, isopropyl 2-bromoacetate and (2'-ethyl)hexyl 2-bromopropionate, sulfonate derivatives, such as sulfonate, p-toluenesulfonate and benzenesulfonate, of ordinary lower aliphatic alcohols and alcohols example for propargyl alcohol, 1-butyne-3-ol, 3-methyl-1-butyne-3-ol, 1-butyne-4-ol, allyl alcohol, methallyl alcohol, 3-methyl-3-butene-1-ol, glycolic acid methyl ester, and methyl lactate.

The phenol derivatives expressed by the formula (V) which are the materials for the production of the compounds of the present invention can be easily produced by treating carbonates derivatives expressed by the following formula:

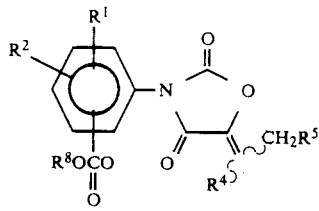

(wherein $R^1$, $R^2$, $R^4$ and $R^5$ denote the same as those described above and $R^8$ denotes a lower alkyl group having 1 to 4 carbon atoms or an aralkyl group having 7 to 10 carbon atoms) in an ordinary organic solvent in the presence of a base (refer to Reference Examples 4 to 12 described below).

In the operation of the reaction of the present invention, the metal salts of the phenol derivatives (when M in the formula (v) is an alkali metal) obtained by the treatment of the compounds expressed by the above-described formula (VII) with a base can be reacted with the compounds expressed by the formula (VI) without isolation from the reaction mixture to produce 1,3-oxazolidine-2,4-dione derivatives expressed by the formula (I').

The oxazolidinedione derivatives expressed by the formula (VII) can be produced by the method described below.

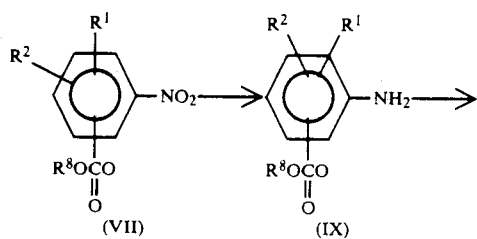

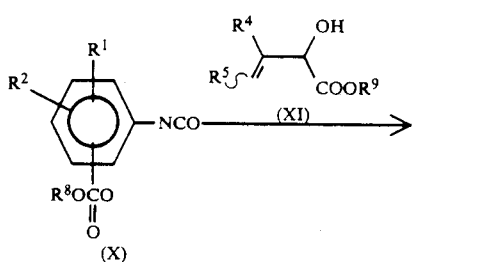

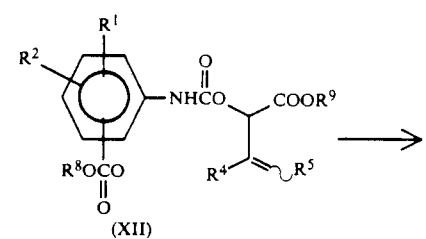

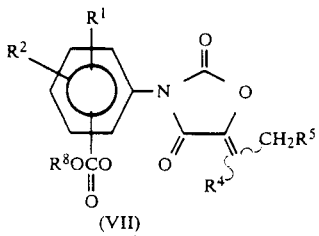

Nitrobenzene derivatives (VIII) (wherein $R^1$ and $R^2$ denote the same as those described above and $R^8$ denotes a lower alkyl or an aralkyl group) are reduced in the presence of a catalyst such as platinum oxide, platinum-carbon or palladium-carbon to form aniline derivatives (IX) (wherein $R^1$, $R^2$ and $R^8$ denote the same as those described above) which can be easily changed into isocyanate derivatives (X) (wherein $R^1$, $R^2$ and $R^8$ denote the same as those described above) by treating with phosgene gas or trichloromethyl chloroformate. These isocyanate derivatives (X) and $\beta,\gamma$-unsaturated glycolic acid esters (XI) (wherein $R^4$ and $R^5$ denote the same as those described above and $R^9$ denotes a lower alkyl group having 1 to 4 carbon atoms) can be then reacted, in some cases, in the presence of a base to lead to carbamate derivatives (XII) (wherein $R^1$, $R^2$, $R^4$, $R^5$, $R^8$ and $R^9$ denote the same as those described above). These carbamate derivatives can then be cyclized by using a tertiary amine such as triethylamine or tributylamine, an inorganic salt such as potassium carbonate or sodium methoxide, or a carboxylic acid salt such as sodium acetate as a base to produce oxazolidinedione derivatives (VII).

The present invention is described in detail below with reference to examples, reference examples and experimental examples. The physical, analytical and spectral data for the compounds synthesized in Example 1 to 38 are shown in Table 2 and 3.

EXAMPLE 1

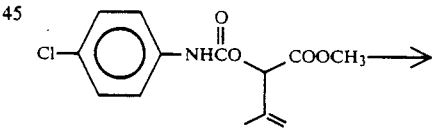

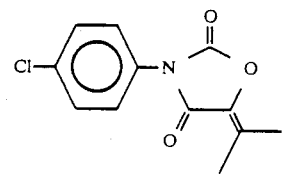

To a benzene solution (50 ml) of methyl 2-{N-(4'-chlorophenyl)carbamoyloxy}-3-methyl-3-butenoate (2.71 g, 10 mmol) was added triethylamine (1.0 ml) and the mixture was heated under reflux for 5 hours. After the removal of the solvent under reduced pressure, methanol was added to the resulting residue to precipitate white crystals of the described product. These crystals (1.87 g) were isolated by filtration and identified as 3-(4'-chlorophenyl)-5-isopropylidene-1,3-oxazolidine-2,4-dione by NMR and IR analysis.

EXAMPLE 2

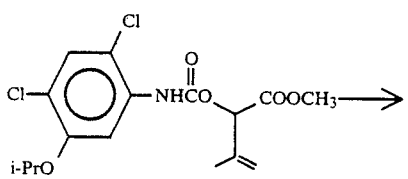

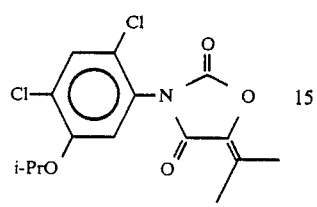

To a benzene solution (50 ml) of 2-{N-(2',4'-dichloro-5'-isopropoxyphenyl)carbamoyloxy}-3-methyl-3-butenoate (1.82 g, 5 mmol) was added sodium methoxide (0.1 g) and the mixture was heated under reflux for 1 hour. After the removal of the solvent under reduced pressure, methanol (20 ml) was added to the resulting residue to precipitate white crystals of the desired product. These crystals (1.10 g) deposited by cooling were isolated by filtration and identified as 3-(2',4'-dichloro-5'-isopropoxyphenyl)-5-isopropylidene-1,3-oxazolidine-2,4-dione by NMR and IR analysis.

EXAMPLE 3

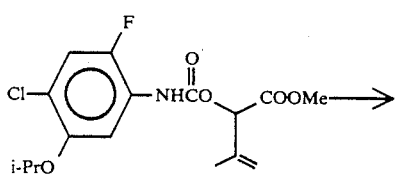

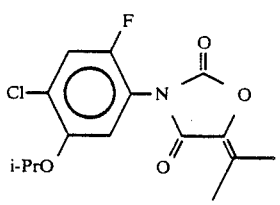

To a toluene solution (50 ml) of methyl 2-{N-(2'-fluoro-4'-chloro-5'-isopropoxyphenyl)carbamoyloxy}-3-methyl-3-butenoate (1.79 g, 5 mmol) was added sodium methoxide (0.1 g) and then the mixture was heated under reflux for 2 hours. After the removal of the solvent under reduced pressure, methanol (20 ml) was added to the resulting residue to precipitate white crystals of the desired product. These crystals (1.87 g) deposited by cooling were isolated
by filtration and identified as 3-(2'-fluoro-4'-chloro-5'-isopropoxyphenyl)-5-isopropylidene-1,3-oxazolidine-2,4-dione by NMR and IR analysis.

EXAMPLE 4

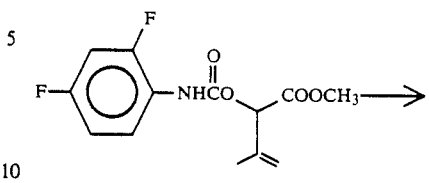

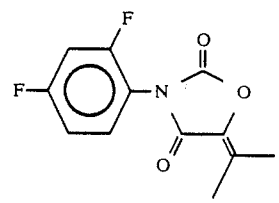

To a toluene solution (30 ml) of methyl 2-{N-(2',4'-difluorophenyl)carbamoyloxy}-3-methyl-3-butenoate (1.43 g, mmol) was added sodium methoxide (50 mg) and then the mixture was heated at reflux for 3 hours. After the removal of the solvent under reduced pressure, methanol (20 ml) was added to the resulting residue to precipitate white crystals of the desired product. These crystals (1.10 g) were isolated by filtration and identified as 3-(2',4'-difluorophenyl)-5-isopropylidene-1,3-oxazolidine-2,4-dione by NMR and IR analysis.

EXAMPLE 5

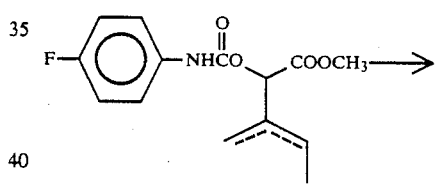

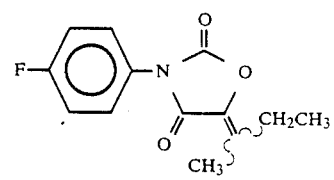

To a benzene solution (30 ml) of a mixture (1.40 g, 5 mmol) methyl 2-{N-(4'-fluorophenyl)carbamoyloxy}-3-ethyl-3-butenoate and 2-{N-(2',4'-dichlorophenyl)carbamoyloxy}-3-methyl-3-pentenoate was added N-methylmorpholine (0.5 ml) and then the mixture was heated at reflux for 3 hours. After the removal of the solvent by distillation, methanol (20 ml) was added to the resulting residue to precipitate white crystals of the desired product. These crystals (0.98 g) were isolated by filtration and identified as 3-(2',4'-dichlorophenyl)-5-(2'-butylidene)-1,3-oxazolidine-2,4-dione by NMR and IR analysis.

EXAMPLES 6 to 10

Oxazolidinedione derivative corresponding to the carbamates described below were synthesized therefrom in a manner similar to that of Example 1.

EXAMPLE 6 methyl 2-{N-(4'-bromophenyl)carbamoyloxy}-3-ethyl-3-butenoate and methyl 2-{N-(4'-bromophenyl)carbamoyloxy}-3-methyl-3-pentenoate

EXAMPLE 7 methyl 2-{N-(2',4'-dichlorophenyl)carbamoyloxy}-3-methyl-3-butenoate

EXAMPLE 8 methyl 2-{N-(4'-fluorophenyl)carbamoyloxy]-3-methyl-3-butenoate

EXAMPLE 9 methyl 2-{N-(4'-chlorophenyl)carbamoyloxy}-3-ethyl-3-butenoate and methyl 2-{N-(4'-chlorophenyl)carbamoyloxy}-3-methyl-3-pentenoate

EXAMPLE 10 methyl 2-{N-(2'-nitro-4'-trifluoromethylphenyl)carbamoyloxy)-3-methyl-3-butenoate

EXAMPLES 11 to 14

Oxazolidinedione derivatives corresponding to the carbamates described below were synthesized therefrom in a manner similar to that of Example 2.

EXAMPLE 11 methyl 2-{N-(2',4'-dichlorophenyl)carbamoyloxy}-3-methyl-3-butenoate

EXAMPLE 12 methyl 2-{N-(2',4',6'-trichlorophenyl)carbamoyloxy}-3-methyl-3-butenoate

EXAMPLE 13 methyl 2-{N-(2',4'-dichlorophenyl)carbamoyloxy]-3-ethyl-3-pentenoate

EXAMPLE 14 methyl 2-{N-(4'-chlorophenyl)carbamoyloxy}-2-(1'-cyclohexenyl) acetate

EXAMPLE 15

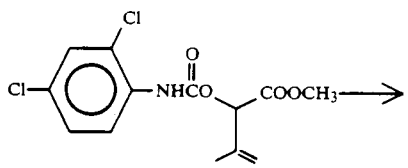

A benzene solution (60 ml) of 2,4-dichlorophenylisocyanate (4.16 g, 22.2 mmol) and methyl 2-hydroxy-3-methyl-3-butenoate (5.72 g, 44 mmol) was heated under reflux for 2.5 hours. It was confirmed by NMR and IR analysis of the reaction mixture that the isocyanate was completely consumed and a carbamate, methyl 2-{N-(2',4'-dichlorophenyl)carbamoyloxy}-3-methyl-3-butenoate, was produced. After the addition of sodium methoxide (100 mg) to the reaction mixture, the solution was further heated under reflux for 5 hours. The solvent was then removed by distillation and methanol (20 ml) was added to the resulting residue to precipitate white crystals of the desired product. These crystals (3.32 g) were isolated by filtration and identified as 3-(2',4'-dichlorophenyl)-5-isopropylidene-1,3-oxazolidine-2,4-dione by NMR and IR analysis.

EXAMPLE 16

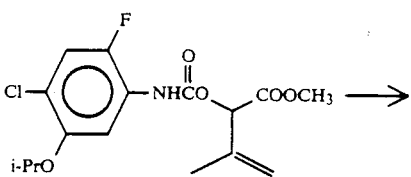

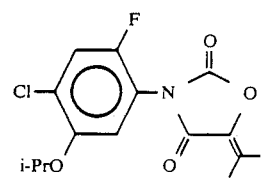

A toluene solution (50 ml) of 2-fluoro-4-chloro-5-isopropoxyphenyl isocyanate (2.30 g, 10 mmol) and methyl 2-hydroxy-3-methyl-3-butenoate (3.0 g, 23 mmol) was stirred at 80° C. for 3 hours. It was confirmed by NMR and IR analysis of the reaction mixture that the isocyanate was completely consumed and a carbamate, methyl 2-{N-(2'-fluoro-4'-chloro-5'-isopropoxyphenyl)carbamoyloxy}-3-methyl-3-butenoate, was produced. After the addition of sodium methoxide (0.1 g) to the reaction mixture, the solution was further heated at reflux for 5 hours. The solvent was then removed under reduced pressure and methanol (10 ml) was added to the resulting residue to precipitate white crystals of the desired product. These crystals (1.49 g) deposited by cooling were isolated by filtration and identified as 3-(2-'-fluoro-4'-chloro-5'-isopropoxyphenyl)-5-isopropylidene-1,3-oxazolidine-2,4-dione by NMR and IR analysis.

EXAMPLE 17

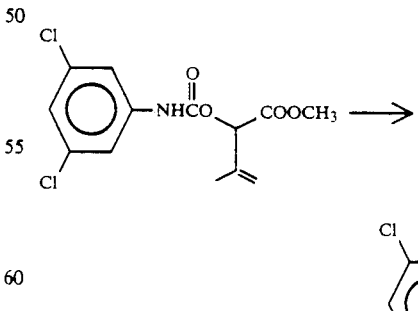

A reaction was effected in the same manner as that in Example 15 except that 3,5-dichlorophenyl isocyanate was used as an isocyanate to give 3-(3',5'-dichlorophenyl)-5-isopropylidene-1,3-oxazolidine-2,4-dione.

EXAMPLE 18

A reaction was effected in the same manner as that in Example 15 except that methyl 2-hydroxy-3-ethyl-3-pentenoate was used as a 2-hydroxy carboxylic acid ester to give 3-(2',4'-dichlorophenyl)-5-(3'-pentylidene)-1,3-oxazolidine-2,4-dione.

EXAMPLE 19

A benzene solution (50 ml) of phenyl isocyanate (1.19 g, 10 mmol) and methyl 2-hydroxy-3-methyl-3-butenoate (2.0 g, 10 mmol) was stirred at room temperature for 2 hours. It was confirmed by NMR and IR analysis of the reaction mixture that the isocyanate was completely consumed and a carbamate, 2-(N-phenylcarbamoyloxy)-3-methyl-3-butenoate, was produced. After the addition of triethylamine to the reaction mixture, the solution was further heated at reflux for 3 hours. The solvent was then removed under reduced pressure and methanol (10 ml) was added to the resulting residue to precipitate white crystals of the desired product. These crystals (1.51 g) were separated by filtration and identified as 3-phenyl-5-isopropylidne-1,3-oxazolidine-2,4-dione by NMR and IR analysis.

EXAMPLES 20 to 26

Carbamates corresponding to the aryl isocyanates and 2-hydroxy carboxylic acid esters described below were synthesized therefrom in a manner similar to that in Example 15 and treated with a base to give the intended oxazolidinedione derivatives.

EXAMPLE 20

2-fluorophenyl isocyanate and methyl 2-hydroxy-3-methyl-3-butenoate

EXAMPLE 20'

4-chlorophenyl isocyanate, methyl 2-hydroxy-3-methyl-3-pentenoate and methyl 2-hydroxy-3-butyl-3butenoate

EXAMPLE 21

4-chlorophenyl isocyanate, methyl 2-hydroxy-3methyl-3-nonenoate and methyl 2-hydroxy-3-hexyl-3-butenoate

EXAMPLE 22

3,4-dichlorophenyl isocyanate and methyl 2-hydroxy-3-methyl-3-butenoate

EXAMPLE 23 phenyl isocyanate and methyl 2-hydroxy-3-ethyl-3-pentenoate

EXAMPLE 24

3,4-dichlorophenyl isocyanate and methyl 2-hydroxy-3-phenyl-3-butenoate

EXAMPLE 25

3,4-dichlorophenyl isocyanate and methyl 2-hydroxy-3-(4'-chlorophenyl)-3-butenoate

EXAMPLE 26 phenyl isocyanate and methyl 2-hydroxy-3-(4'-chlorophenyl)-3-butenoate

EXAMPLE 27 to 31

Carbamates corresponding to the aryl isocyanates and 2-hydroxy carboxylic acid esters described below were synthesized therefrom in a manner similar to that of Example 19 and treated with a base to give the intended oxazolidinedione derivatives.

EXAMPLE 27

4-chlorophenyl isocyanate and methyl 2-hydroxy-3-ethyl-3-pentenoate

EXAMPLE 28

4-fluorophenyl isocyanate and methyl 2-hydroxy-3-methyl-3-butenoate

EXAMPLE 29

3,5-dichlorophenyl isocyanate and methyl 2-hydroxy-3-(4'-chlorophenyl)-3-butenoate

EXAMPLE 30

4-chlorophenyl isocyanate and methyl 2-hydroxy-3-methyl-3-butenoate

EXAMPLE 31

4-fluorophenyl isocyanate, methyl 2-hydroxy-3-ethyl-3-pentenoate and methyl 2-hydroxy-3-ethyl-3-butenoate

EXAMPLE 32

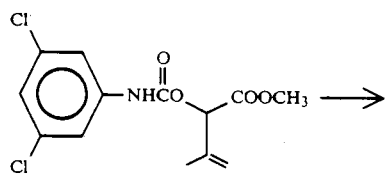

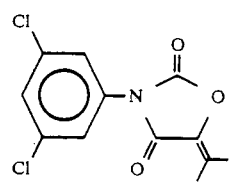

To a benzene solution (50 ml) of a mixture of methyl 2-hydroxy-3-methyl-3-butenoate (1.30 g, 10 mmol) and N-(3,5-dichlorophenyl)carbamoyl chloride prepared from 3,5-dichloroaniline (3.24 g, 20 mmol) and trichloromethyl chloroformate was added triethylamine (2 ml), the mixture was stirred at ambient temperature for 3 hours. After the removal of salts of triethylammonium chloride by filtration, the solvent and excess triethylamine were evaporated from the filtrate under reduced pressure. It was confirmed from the NMR and IR analysis of the resulting residue that methyl 2-{N-(3',5'-dichlorophenyl)carbamoyloxy}-3-methyl-3-butenoate was produced. To a solution of the residue was added sodium methoxide (50 mg) and the mixture was further heated at reflux for 3 hours. After the reaction was completed the solvent was removed from the reaction mixture under reduced pressure, and then 0.1N hydrochloric acid was added to the residue. The product was extracted from the acidic solution with ether. The ethereal extracts were combined, dried and evaporated as small a volume as possible and then methanol was added to the resulting oily product to precipitate white crystals of the desired product. These crystals (1.80 g) were isolated by filtration and identified as 3-(3',5'-dichlorophenyl)-5-isopropylidene-1,3-oxazolidine-2,4-dione.

EXAMPLE 33

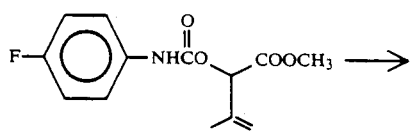

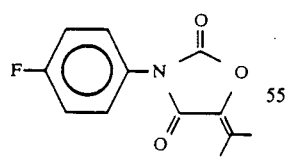

To a benzene solution (50 ml) of a mixture of methyl 2-hydroxy-3-methyl-3-butenoate (1.30 g, 10 mmol) and N-(4-fluorophenyl)carbamoyl chloride prepared from 4-fluorophenylaniline (2.22 g, 20 mmol) and trichloromethyl chloroformate was added triethylamine (2 ml) and the mixture was stirred at ambient temperature for 3 hours. After the reaction mixture was further heated at reflux for 3 hours, the solvent was completely removed by distillation, and then 0.1N hydrochloric acid was added to the resulting residue. The product was extracted from the acidic solution with ether. The ethereal extracts combined, dried and evaporated as small a volume as possible and then methanol was added to the oily product obtained to precipitate white crystals of the pure product. These crystals (1.80 g) deposited by cooling were separated by filtration and identified as 3-(4'-fluorophenyl)-5-isopropylidene-1,3-oxazolidine-2,4-dione by spectral analysis.

EXAMPLE 34

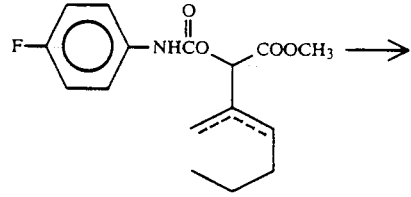

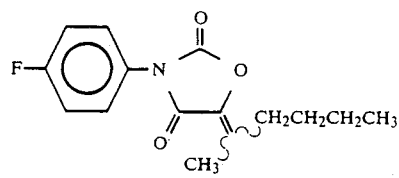

A reaction was effected in a way same as that of Example 27 except that a mixture of methyl 2-hydroxy-3-methyl-3-butenoate and methyl 2-hydroxy-3-methyl-3-pentenoate was used as a 2-hydroxy carboxylic acid ester to give 3-(4'-fluorophenyl)-5-isobutylidene-1,3-oxazolidine-2,4-dione (0.41 g).

EXAMPLE 35

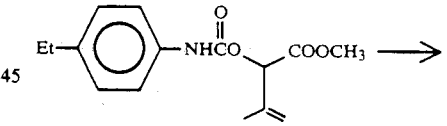

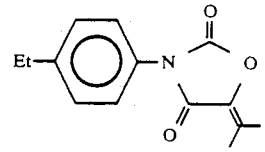

To a benzene solution (50 ml) of 4-ethylphenyl isocyanate prepared from 4-ethylphenylaniline (3.63 g, 30 mmol) and trichloromethyl chloroformate was added ethyl 2-hydroxy-3-methyl-3-butenoate (3.6 g, 25 mmol), and then the mixture was heated at reflux in the pressure of pyridine (1.0 ml). After 2 hours, the solvent was completely removed by distillation. Methanol was added to the resulting residue and the white crystals (3.3 g) deposited were isolated by filtration. These crystals were identified as 3-(4'-ethylphenyl)-5-isopropylidene-1,3-oxazolidine-2,4-dione by NMR and IR analysis.

EXAMPLE 36

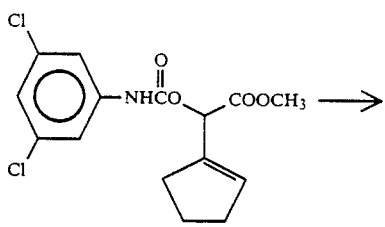

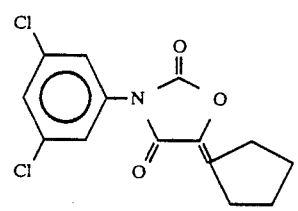

To a benzene solution (30 ml) of 3,5-dichlorophenyl isocyanate (1.88 g, 10 mmol) was added methyl 2-hydroxy-3-cyclopentenyl acetate (1.95 g, 15 mmol), and the mixture was stirred at ambient temperature. It was confirmed by spectral analysis of the reaction mixture that the isocyanate was completely consumed and a desired carbamate was produced. After the addition of triethylamine (0.5 ml), the reaction mixture was then heated under reflux for 3 hours. The solvent was removed completely and methanol was added to the resulting residue to precipitate white crystals of the desired product. These crystals (1.24 g) were separated by filtration and identified as 3-(3',5'-dichlorophenyl)-5-isopropylidene-1,3-oxazolidine-2,4-dione by NMR and IR analysis.

EXAMPLE 37

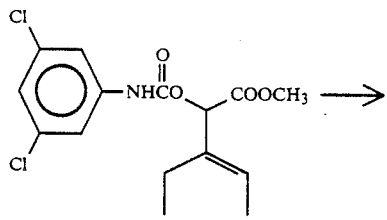

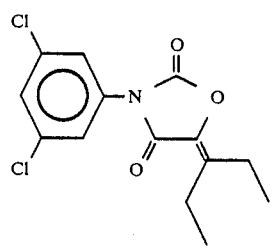

A reaction was effected in the same manner as that in Example 36, except that the 2-hydroxy carboxylic acid ester was methyl 2-hydroxy-3-ethyl-3-pentenoate, to give 3-(3',5'-dichlorophenyl)-5-(3'-pentylidine)-1,3-oxazolidine-2,4-dione.

EXAMPLE 38

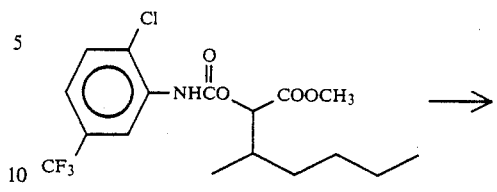

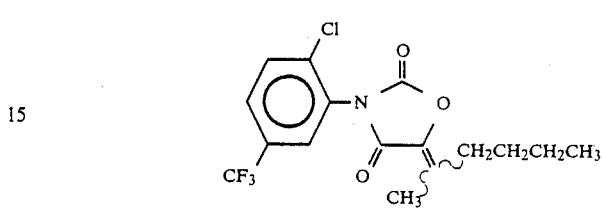

To a toluene solution (30 ml) of a mixture of methyl 2-{N-(2'-chloro-5'-trifluoromethylphenyl)carbamoyloxy}-3-methyl-3-heptenoate and 3-butyl-3-butenoate (1.97 g, 5 mmol) was added potassium t-butoxide (50 mg), and the mixture was heated under reflux for 2 hours. After the reaction was completed, the solvent was removed by distillation. Methanol was then added to the resulting residue followed by cooling to precipitate white crystals of the desired product. These crystals (0.85 g) deposited were isolated by filtration and identified as 3-(2'-chloro-5'-trifluoromethylphenyl)-5-(2'-hexylidene)-1,3-oxazolidine-2,4-dione by means of NMR and IR analysis.

The starting compounds of the above-described Examples 1 to 38 were produced in accordance with Reference Examples 1 to 4 described below.

REFERENCE EXAMPLE 1

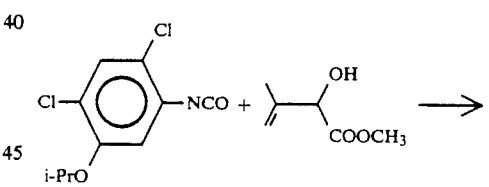

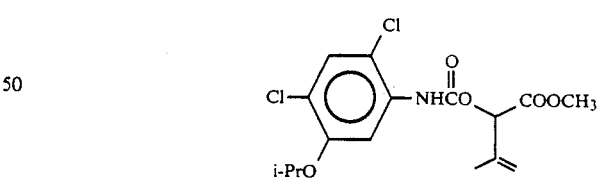

A benzene solution (20 ml) of 2,4-dichloro-5-isopropoxyphenyl isocyanate (1.72 g, 7 mmol) and methyl 2-hydroxy-3-methyl-3-butenoate (1.04 g, 8 mmol) was heated at reflux for 2 hours. The resulting mixture was subjected to separating purification using a silica gel column to give 2-{N-(2',4'-dichloro-5'-isopropoxyphenyl)carbamoyloxy}-3-methyl-3-butenoate (0.67 g) as a colorless oil.

$^1$H-NMR (CDCl$_3$, TMS, ppm): δ 1.37 (d,6H,J=6 Hz), 1.82 (d,3H,J=1.5 Hz), 3.72(s,3H), 4.53(sept, 1H,J=6 Hz), 5.07(q,1H,J=1.5 Hz), 5.17(br,s,1H), 5.30(s,1H), 7.13(br,s,1H), 7.25(s,1H), 7.87(s,1H).

IR (neat, cm$^{-1}$): 3350, 1740, 1410, 1210, 860.

REFERENCE EXAMPLE 2

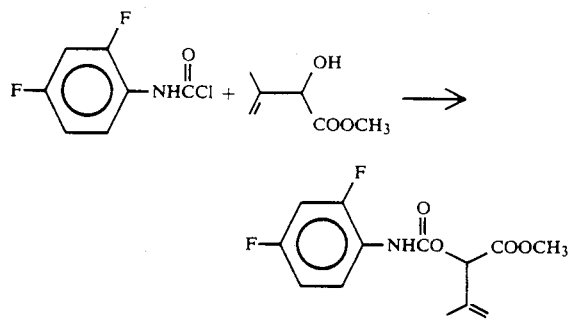

To a benzene solution (30 ml) of a mixture of N-(2,4-difluorophenyl)carbamoyl chloride (2.58 g, 20 mmol) was added methyl 2-hydroxy-3-methyl-3-butenoate (3.0 g, 23 mmol) and N-methylmorpholine (2.5 ml), and the mixture was stirred at room temperature for 3 hours. After the reaction was completed, the resulting mixture was quenched with water. The organic layer separated was dried and concentrated by distillation. The residue obtained was subjected to separating purification using a silica gel column to give 2-{N-(2',4'-difluorophenyl)-carbamoyloxy}-3-methyl-3-butenoate (3.99 g).

$^1$H-NMR (CDCl$_3$, TMS, ppm): δ 1.80(d,3H), 3.71(s,3H), 5.03(q,1H), 5.15(s,1H), 5.30(d,1H), 6.78(m,2H), 7.07(br,s,1H), 8.03(m,1H).

IR (neat, cm$^{-1}$) 3350, 1740, 1430, 1220, 850.

REFERENCE EXAMPLE 3

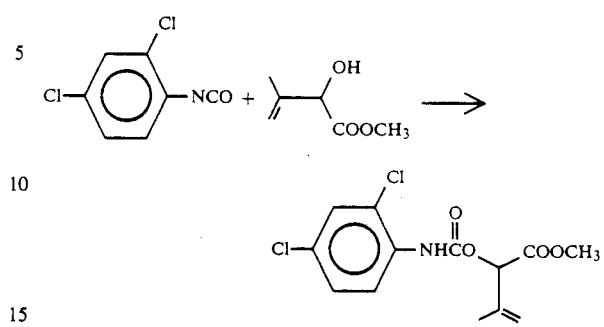

A toluene solution (80 ml) of a mixture of 2,4-dichlorophenyl isocyanate (3.80 g, 20.2 mmol) and methyl 2-hydroxy-3-methyl-3-butenoate (3.05 g, 23.5 mmol) was heated under reflux for 5 hours. The reaction mixture was purified using a silica gel column to give 2-{N-(2',4'-dichlorophenyl)carbamoyloxy}-3-methyl-3-butenoate (4.02 g) as a colorless oil.

$^1$H-NMR (CDCl$_3$, TMS, ppm): δ 1.85(d,3H), 3.78(s,3H), 5.23(q,1H), 5.23(br,s,1H), 5.48(s,1H), 7.12(m,1H), 7.35(m,2H), 8.13(d,1H).

IR (neat, cm$^{-1}$) 3350, 1738, 1420, 1215, 855.

TABLE 2

Physical and Analytical Data for Oxazolidinedione Derivatives

| Compound No.[1] | Example No. | m.p. (°C.) | Formula | Found (Calculated) C (%) | H (%) | N (%) |
|---|---|---|---|---|---|---|
| 1 | 19 | 91–93.5 | C$_{12}$H$_{11}$NO$_3$ | 66.09 (66.35) | 5.00 (5.10) | 6.40 (6.45) |
| 2 | 23 | 51–53 | C$_{14}$H$_{15}$NO$_3$ | 68.30 (68.56) | 6.13 (6.16) | 5.68 (5.71) |
| 3* | 26 | 136–140.5 | C$_{17}$H$_{12}$ClNO$_3$ | 65.12 (65.08) | 3.60 (3.86) | 4.22 (4.46) |
| 4 | 1, 30 | 135–135.5 | C$_{12}$H$_{10}$ClNO$_3$ | 57.09 (57.27) | 3.89 (4.01) | 5.55 (5.57) |
| 5 | 8, 28, 33 | 117–119 | C$_{12}$H$_{10}$FNO$_3$ | 61.28 (61.47) | 4.29 (4.38) | 5.95 (5.84) |
| 6 | 20 | 90.5–91.2 | C$_{12}$H$_{10}$FNO$_3$ | 60.92 (61.28) | 4.26 (4.29) | 5.89 (5.95) |
| 7* | 9 | 79–111 | C$_{13}$H$_{12}$ClNO$_3$ | 58.69 (58.77) | 4.47 (4.55) | 5.22 (5.27) |
| 8* | 6 | 103–107 | C$_{13}$H$_{12}$BrNO$_3$ | 50.43 (50.35) | 3.88 (3.90) | 4.49 (4.52) |
| 9* | 5, 31, 34 | 66.5–70.0 | C$_{13}$H$_{12}$FNO$_3$ | 62.65 (62.46) | 4.85 (5.02) | 5.62 (5.61) |
| 10* | 20' | 57.8–67.0 | C$_{13}$H$_{10}$ClNO$_3$ | 61.46 (61.33) | 5.48 (5.49) | 4.70 (4.77) |
| 11* | 21 | 54.5–56.5 | C$_{17}$H$_{20}$ClNO$_3$ | 63.21 (63.45) | 6.30 (6.26) | 4.24 (4.35) |
| 12 | 27 | 100–102 | C$_{14}$H$_{14}$ClNO$_3$ | 59.93 (60.11) | 5.03 (5.04) | 4.95 (5.01) |
| 13 | 14 | 95–98 | C$_{15}$H$_{14}$ClNO$_3$ | 61.62 (61.76) | 4.87 (4.84) | 4.65 (4.80) |
| 14 | 22 | 146–149 | C$_{15}$H$_9$Cl$_2$NO$_3$ | 50.34 (50.38) | 2.86 (3.18) | 4.84 (4.90) |
| 15 | 17, 32 | 109–115 | C$_{12}$H$_9$Cl$_2$NO$_3$ | 49.16 (50.38) | 3.50 (3.07) | 4.69 (4.75) |
| 16 | 7, 11, 15 | 108–108.5 | C$_{12}$H$_9$Cl$_2$NO$_3$ | 50.30 (50.38) | 3.18 (3.17) | 4.88 (4.89) |
| 17* | 13, 18 | 49–51 | C$_{14}$H$_{13}$Cl$_2$NO$_3$ | 53.26 (53.52) | 4.22 (4.17) | 4.33 (4.46) |
| 18 | 37 | 80–81 | C$_{14}$H$_{13}$Cl$_2$NO$_3$ | 53.36 (53.52) | 4.13 (4.17) | 4.44 (4.46) |
| 19 | 38 | 99–104 | C$_{14}$H$_{11}$Cl$_2$NO$_3$ | 53.50 (53.87) | 3.40 (3.55) | 4.41 (4.49) |
| 20* | 24 | 163.5–164 | C$_{17}$H$_{11}$Cl$_2$NO$_3$ | 58.53 (58.64) | 3.10 (3.18) | 3.98 (4.02) |
| 21* | 25 | 153.3–168.5 | C$_{17}$H$_{10}$Cl$_3$NO$_3$ | 53.16 (53.36) | 2.66 (2.63) | 3.65 (3.66) |
| 22* | 29 | 180–185 | C$_{17}$H$_{10}$Cl$_3$NO$_3$ | 53.75 (53.36) | 2.45 (2.63) | 3.50 (3.66) |
| 23* | 4 | 114–114.5 | C$_{12}$H$_9$F$_2$NO$_3$ | 56.10 (56.92) | 3.79 (3.53) | 5.20 (5.53) |
| 24 | 12 | 117–182 | C$_{12}$H$_8$Cl$_3$NO$_3$ | 44.78 (44.96) | 2.36 (2.52) | 4.23 (4.37) |
| 25 | 35 | 116–119 | C$_{14}$H$_{15}$NO$_3$ | 69.05 (68.56) | 6.50 (6.16) | 6.33 (5.71) |
| 26 | 2 | 136–138 | C$_{15}$H$_{15}$Cl$_2$NO$_4$ | 51.82 (52.35) | 4.37 (4.39) | 3.93 (4.07) |
| 27 | 3, 16 | 88–90.5 | C$_{15}$H$_{15}$FClNO$_4$ | 54.75 (54.97) | 4.62 (4.61) | 4.20 (4.27) |
| 28 | 10 | 88–90 | C$_{13}$H$_9$F$_3$N$_2$O$_5$ | 46.54 (47.28) | 2.86 (2.75) | 8.42 (8.48) |
| 29 | 38 | 124–131 | C$_{16}$H$_{15}$F$_3$ClNO$_3$ | 53.38 (53.12) | 4.32 (4.18) | 3.86 (3.87) |

[1]The compounds asterisked are mixtures of cis and trans isomers with respect to the stereochemistry of the double bonds at the 5-positions of the oxazolidinedione rings.

TABLE 3

$^1$H-NMR and IR Spectral Data for Oxazolidinedione Derivatives

| Compound No.[1] (Example No.) | $^1$H-NMR (CDCl$_3$, ppm) | IR (cm$^{-1}$) |
|---|---|---|
| 1 (19) | 2.03(s,3H), 2.26(s,3H), 7.12(s,5H) | 1810, 1728, 1685 |
| 2 (23) | 1.15 and 1.17(each t, total 6H), 2.45(q,2H), 2.77(q,2H), 7.40(m,5H) | 1820 1732 1685 |

TABLE 3-continued

1H-NMR and IR Spectral Data for Oxazolidinedione Derivatives

| Compound No.[1] (Example No.) | 1H-NMR (CDCl3, ppm) | IR (cm$^{-1}$) |
|---|---|---|
| 3* (26) | 2.60(s,3H), 7.47(m,9H) | 1804, 1728, 1632 |
| 4 (1, 30) | 2.05(s,3H), 2.30(s,3H), 7.43(s,4H) | 1813, 1730, 1685 |
| 5 (8, 28, 33) | 2.03(s,3H), 2.28(s,3H), 7.30(m,4H) | 1819, 1722, 1683 |
| 6 (20) | 2.02(s,3H), 2.24(s,3H), 7.10–7.50(m,4H) | 1820, 1736, 1685 |
| 7* (9) | 1.12 and 1.15(each t, total 3H), 2.00 and 2.23(each s, total 3H), 2.37 and 2.70(each q, total 2H), 7.39(s,4H) | 1820, 1740, 1688 |
| 8* (6) | 1.15 and 1.18(each t, total 3H), 2.02 and 2.26(each s, total 3H), 2.38 and 2.72(each q, total 2H), 7.38(d,2H), 7.58(d,2H) | 1823, 1740, 1690 |
| 9* (5, 31, 34) | 1.17(t,3H), 2.03 and 2.28(each s, total 3H), 2.42 and 2.75(each q, total 2H), 7.14(dd,2H), 7.43(m,2H) | 1818, 1728, 1690 |
| 10* (20') | 0.95(m,3H), 1.2–1.37 (m,4H), 1.83 and 2.23 (each s, total 3H), 2.13–2.60(m,2H), 7.38(s,4H) | 1820, 1730, 1685 |
| 11* (21) | 0.92(t,3H), 1.35(m,8H), 1.68 and 2.23(each s, total 3H), 2.0–2.4 (m,2H), 7.43(s,4H) | 1817, 1730, 1690 |
| 12 (27) | 1.13 and 1.15(each t, total 6H), 2.40(q,2H), 2.72(q,2H), 7.43(s,4H) | 1805, 1730, 1680 |
| 13 (14) | 1.67(m,6H), 2.45(t,2H), 2.84(t,2H), 7.39(s,4H) | 1818, 1730, 1681 |
| 14 (22) | 2.05(s,3H), 2.30(s,3H), 7.33–7.66(m,3H) | 1814, 1735, 1688 |
| 15 (17, 32) | 2.05(s,3H), 2.28(s,3H), 7.37(t,1H), 7.50(d,2H) | 1812, 1743, 1683 |
| 16 (7, 11, 15) | 2.07(s,3H), 2.29(s,3H), 7.28(dd,1H), 7.41(dd,1H), 7.58(d,1H) | 1824, 1746, 1695 |
| 17 (13, 18) | 1.08 and 1.10(each t, total 6H), 2.37(q,2H), 2.71(q,2H), 7.20(d,1H), 7.37(dd,1H), 7.56(d,1H) | 1805, 1730, 1678 |
| 18 (37) | 1.16(t,3H), 2.43(q,2H), 2.86(q,2H), 7.40(m,1H), 7.48(d,2H) | 1820, 1739, 1672 |
| 19 (36) | 1.85(m,4H), 2.5–2.95 (m,4H), 7.35–7.60(m,3H) | 1810, 1750, 1700 |
| 20* (24) | 2.67(s,3H), 7.3–7.7(m,8H) | 1803, 1728, 1653 |
| 21* (25) | 2.30 and 2.60 (each s, total 3H), 7.2–7.65(m,7H) | 1805, 1726, 1635 |
| 22* (29) | 2.62(s,3H), 7.3–7.6(m,7H) | 1804, 1720, 1633 |
| 23* (4) | 2.03(s,3H), 2.25(s,3H), 6.90–7.5(m,3H) | 1822, 1740, 1692 |
| 24 (12) | 2.08(s,3H), 2.30(s,3H), 7.48(s,2H) | 1810, 1753, 1685 |
| 25 (35) | 1.60(t,3H), 1.98(s,3H), 2.33(s,3H), 2.67(q,2H), 7.25(m,4H) | 1814, 1726, 1685 |
| 26 (2) | 1.38(d,6H), 2.07(s,3H), 2.28(s,3H), 4.53(sept,1H) 6.96(s,1H), 7.62(s,1H) | 1820, 1745, 1695 |
| 27 (3, 16) | 1.38(d,6H), 2.06(s,3H), 2.28(s,3H), 4.44(sept,1H), 0.85(d,1H), 7.28(d,1H) | 1813, 1746, 1695 |
| 28 | 2.08(s,3H), 2.27(s,3H), | 1817 |
| (10) | 7.65(d,1H), 8.03(dd,1H), 8.42(d,1H) | 1742, 1692 |
| 29 (38) | 0.97(t,3H), 1.48(m,4H), 2.05(s,3H), 2.70(m,3H), 7.58(br s,1H), 7.68(d,2H) | 1825, 1750, 1687 |

[1]The compounds asterisked are mixtures of cis and trans isomers with respect to the stereochemistry of the double bonds at the 5-positions of the oxazolidinedione rings.

Other production methods of the present invention will be described below with reference to Examples 39 to 46.

EXAMPLE 39

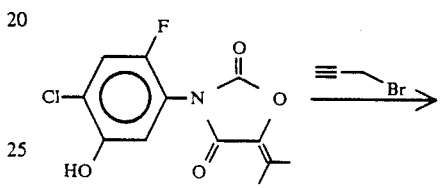

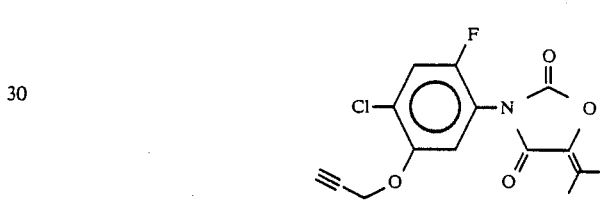

To an acetonitrile solution (30 ml) of 3-(2'-fluoro-4'-chloro-5'-hydroxyphenyl)-5-isopropylidene-1,3-oxazolidine-2,4-dione (0.72 g, 2.5 mmol) was added sodium carbonate (0.16 g), and the mixture was heated at reflux for 1 hour. After the addition of propargyl bromide (0.36 g, 3.0 mmol), the reaction mixture was further refluxed for 1 hour. After the solution was quenched with 0.1N hdyrochloric acid, the product was extracted with chloroform. The extracts combined were dried and evaporated as small a volume as possible. The resulting pale yellow oil was purified by silica gel column chromatography to give pure 3-(2'-fluoro-4'-chloro-5'-propargyloxyphenyl)-5-isopropylidene-1,3-oxazolidine-2,4-dione. (0.53 g, 65% yield).

EXAMPLE 40

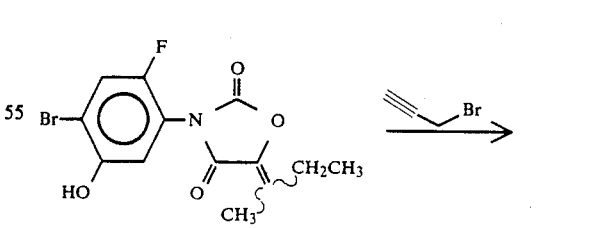

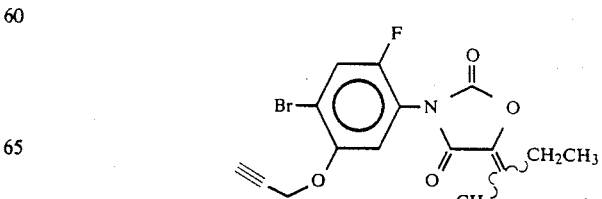

To an acetonitrile solution (25 ml) of 3-(2'-fluoro-4'-bromo-5'-hydroxyphenyl)-5-(sec-butylidene)-1,3-oxazolidine-2,4-dione (0.26 g, 0.82 mmol) was added potassium carbonate (0.11 g) and the mixture was heated at reflux for 1 hour. After the addition of propargyl bromide (0.1 g, 0.83 mmol), the reaction mixture was further refluxed for 1 hour. 3-(2'-fluoro-4'-bromo-5'-propargyloxyphenyl)-5-(sec-butylidene)-1,3-oxazolidine-2,4-dione (0.24 g, 77% yield) was obtained by an operation similar to that of Example 1.

EXAMPLE 41

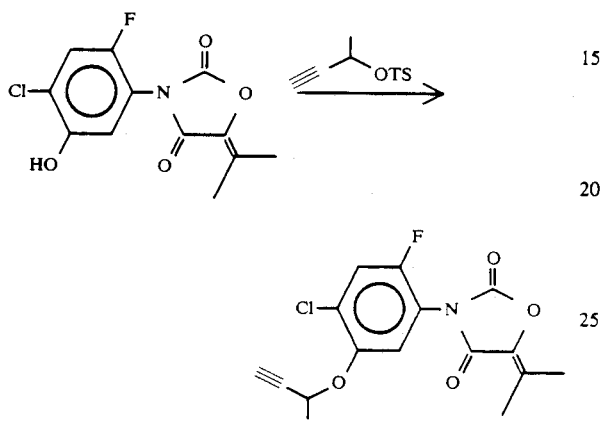

To an acetonitrile solution (30 ml) of a mixture of 3-(2'-fluoro-4'-chloro-5'-hydroxyphenyl)-5-isopropylidene-1,3-oxazolidine-2,4-dione (0.57 g, 2.0 mmol) and potassium carbonate (0.27 g) was added p-toluenesulfonate of 1-butyne-3-ol (0.5 g, 2.2 mmol) and a catalytic amount of benzyltriethylammonium bromide (ca. 20 mg), and the mixture was heated at reflux for 15 hours. After the reaction was completed, ether was added to the reaction mixture and the solution was washed with 1N hydrochloric acid. The organic layer was dried and then evaporated as small a volume as possible. The resulting brownish residue was purified by silica gel column chromatography to give 3-{2'-fluoro-4'-chloro-5'-(1''-methylpropargyloxy)phenyl}-5-isopropylidene-1,3-oxazolidine-2,4-dione. (0.34 g, 50% yield).

EXAMPLE 42

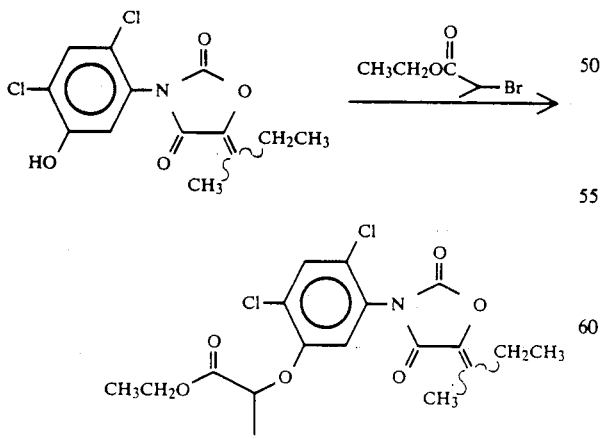

To an acetonitrile solution (30 ml) of a mixture of 3-(2',4'-dichloro-5'-hydroxyphenyl)-5-(sec-butylidene)-1,3-oxazolidine-2,4-dione (1.58 g, 5 mmol) was added potassium carbonate (0.69 g), and the mixture was heated at reflux for 2 hours. After the addition of ethyl 2-bromopropionate (0.93 g, 5.1 mmol), the reaction mixture was further refluxed for 1 hour. Ether was added to the reaction mixture and the solution was washed with 1N hydrochloric acid and extracted with ether. The ethereal extracts combined were dried and then evaporated as small a volume as possible. The resulting residue was purified by silica gel column chromatography to give 3-(2',4'-dichloro-5'-(1''-ethoxycarobylethoxyloxy)phenyl}-5-(sec-butylidene)-1,3-oxazolidine-2,4-dione. (1.51 g, 73% yield)

EXAMPLE 43

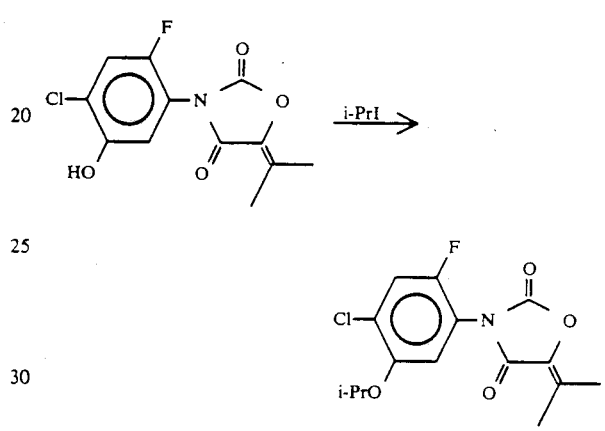

An acetonitrile solution (50 ml) of a mixture of 3-(2'-fluoro-4'-chloro-5'-hydroxyphenyl)-5-isopropylidene-1,3-oxazolidine-2,4-dione (2.85 g, 10 mmol), isopropyl iodide (3 ml) and potassium carbonate (3.5 g) was heated under reflux for 3 hours. After the reaction was completed the solvent was removed under reduced pressure. The resulting mixture was quenched with 1N hydrochloric acid and extracted with ether. The ethereal extracts combined were dried and evaporated as small a volume as possible. Methanol was added to the resulting residue to precipitate crystals of the desired product. These crystals deposited were isolated by filtration and identified as 3-(2'-fluoro-4'-chloro-5'-isopropoxyphenyl)-5-isopropylidene-1,3-oxazolidine-2,4-dione. (3.10 g, 95% yield)

EXAMPLE 44

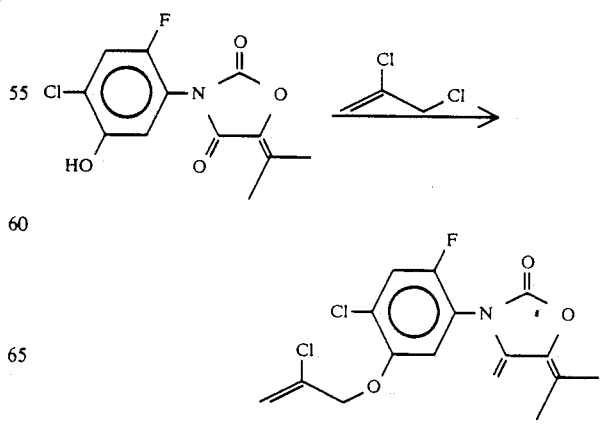

To an N,N-dimethylformamide solution (10 ml) of 3-(2'-fluoro-4'-chloro-5'-hydroxyphenyl)-5-isopropylidene-1,3-oxazolidine-2,4-dione (1.75 mg, 0.61 mmol) was added potassium carbonate (42 mg), and the mixture was stirred for 3 hours at room temperature. 2,3-Dichloro-1-propene (0.5 ml) was then added to the mixture which was further stirred for 1 hour at room temperature. After the removal of the solvent under reduced pressure, the reaction mixture was quenched with 0.1N hydrochloric acid and extracted with ether. The ethereal extracts combined were dried and concentrated under reduced pressure as small a volume as possible. Methanol was added to the resulting residue, followed by cooling. The white crystals deposited were isolated by filtration and identified as 3-{2'-fluoro-4'-chloro-5'-(2''-chloroallyloxy)phenyl}-5-isopropylidene-1,3-oxazolidine-2,4-dione. (80 mg, 36% yield)

EXAMPLE 45

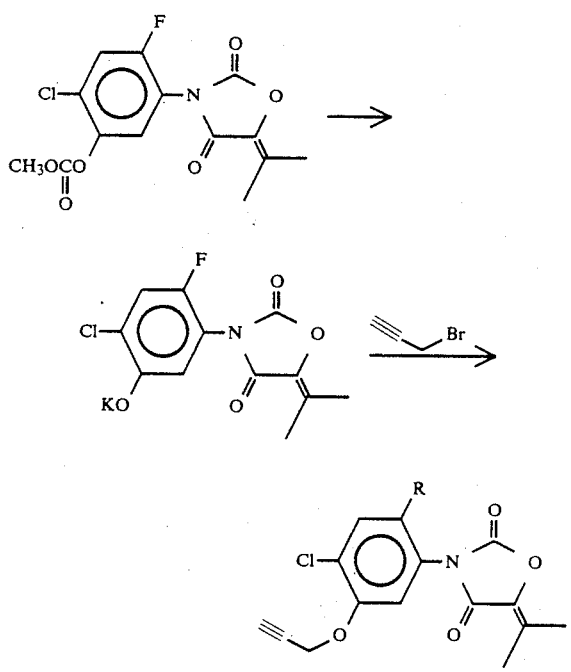

To a methanol solution (50 ml) of 3-(2'-fluoro-4'-chloro-5'-methoxycarbonyloxyphenyl)-5-isopropylidene-1,3-oxazolidine-2,4-dione (3.43 g, 10 mmol) was added potassium carbonate (1.38 g, 10 mmol), and the mixture was heated at reflux for 1 hour. After the removal of the solvent under reduced pressure, acetonitrile (50 ml) was added to the resulting mixture. Propargyl bromide (5 ml) was added to the mixture which was further stirred for 2 hours at room temperature. The reaction mixture was treated in a manner similar to that of Example 1 and purified by silica gel column, chromatography to give 3-(2'-fluoro-4'-chloro-5'-propargyloxyphenyl)-5-isopropylidene-1,3-oxazolidine-2,4-dione. (0.89 g, 28% yield).

EXAMPLE 46

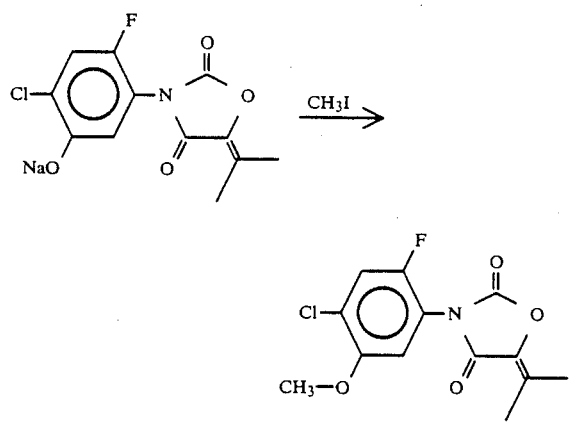

A ca. 60% sodium hydride dispersion in mineral oil (5.0 mmol) was washed with hexane and the solvent was removed. Dried tetrahydrofuran (10 ml) was added. To the suspension of sodium hydride in tetrahydrofuran was added 3-(2'-fluoro-4'-chloro-5'-hydroxyphenyl)-5-isopropylidene-1,3-oxazolidine-2,4-dione (1.43 g, 5 mmol), and the mixture was stirred at room temperature until the evolution of hydrogen was stopped. A white solid of sodium salt of starting material was obtained by the removal of the solvent. Methyl iodide (1 ml) was added to the acetonitrile solution (10 ml) of the sodium salt and then the mixture was heated for 3 hours. After the reaction was completed, the resulting mixture was quenched with 0.1N hydrochloric acid and extracted with chloroform. The extracts combined were dried and evaporated to give a pale yellow oil. Methanol was added and cooled to precipitate white crystals of the desired product. These crystals were isolated and identified as 3-(2'-fluoro-4'-chloro-5'-methoxyphenyl)-5-isopropylidene-1,3-oxazolidine-2,4-dione. (1.42 g, 95% yield)

Compounds 30 to 56 shown in Table 1 were synthesized in accordance with the methods of Examples 39 to 46. The physical and spectral data of the obtained compounds are shown in Table 4 and 5.

The production of the starting compounds used in Examples 39 to 46 is described below with reference to Reference Examples 4 to 11.

REFERENCE EXAMPLE 4

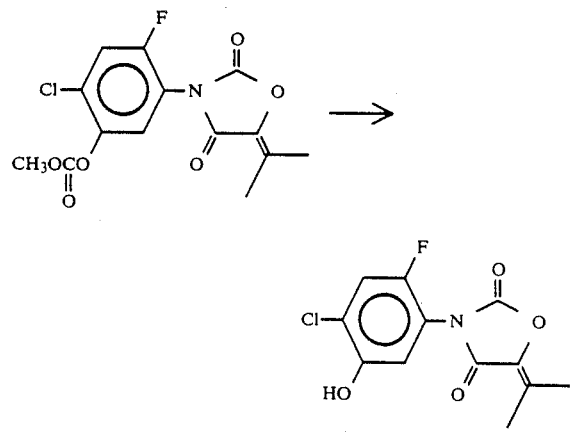

To a dried methanol solution (100 ml) of 3-(2'-fluoro-4'-chloro-5'-methoxycarbonyloxyphenyl)-5-isopropylidene-1,3-oxazolidine-2,4-dione (3.44 g, 10 mmol), which was synthesized by a method shown in Reference Example 12 described below, was added potassium carbonate (1.38 g, 10 mmol) and the mixture was heated at reflux for 2 hours. After the reaction was completed, the resulting mixture was quenched with an aqueous solution of ammonium chloride and extracted with ether. The ethereal extracts were dried and evaporated as small a volume as possible. The resulting residue was purified by silica gel column chromatography to give pure 3-(2'-fluoro-4'-chloro-5'-hydroxyphenyl)-5-isopropylidene-1,3-oxazolidine-2,4-dione (1.60 g).

$^1$H-NMR (CDCl$_3$, TMS, ppm): δ 2.06(3H,s), 2.29(3H,s), 5.78(1H,br s), 6.98(1H,d), 7.25(d,1H)

IR (KBr disk, cm$^{-1}$): 3425, 1820, 1738, 1685.

m.p.: 133°–135° C.

REFERENCE EXAMPLE 5

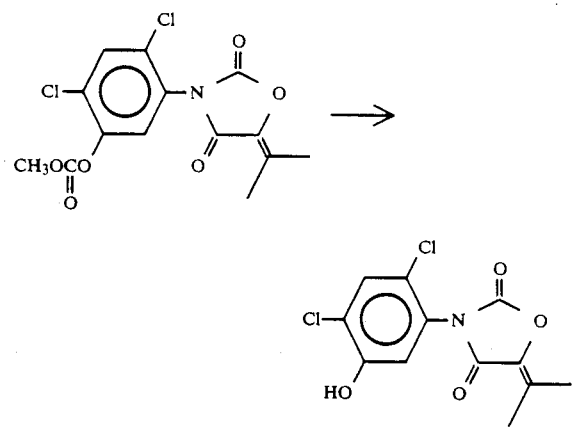

To a dried methanol solution (100 ml) of 3-(2',4'-dichloro-5'-methoxycarbonyloxyphenyl)-5-isopropylidene-1,3-oxazolidine-2,4-dione (3.60 g, 10 mmol), which was synthesized from 2,4-dichloro-5-methoxycarbonyloxy nitrobenzene as a starting material in a method similar to that shown in Reference Example 6, 9, 10 and 4, was added potassium carbonate (0.69 g, 5 mmol) and the mixture was heated under reflux for 2 hours. 3-(2',4'-dichloro-5'-hydroxyphenyl)-5-isopropylidene-1,3-oxazolidine-2,4-dione (1.72 g) was obtained by a treatment similar to that in Reference Example 1.

$^1$H-NMR (CDCl$_3$, TMS, ppm): δ 2.03(3H,s), 2.27(3H,s), 6.90(1H,s), 7.48(1H,s)

IR (KBr disk, cm$^{-1}$) 3400, 1820, 1739, 1690.

m.p.: 166°–168° C.

REFERENCE EXAMPLE 6

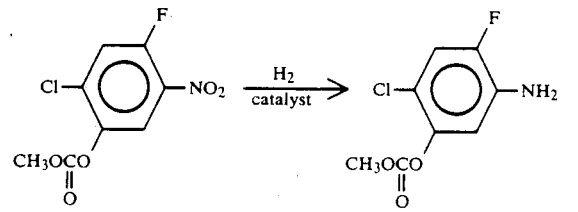

To an ethanol solution (600 ml) of 2-fluoro-4-chloro-5-methoxycarbonyloxy nitrobenzene (52.1 g, 0.24 mol) was added platinum dioxide (1.5 g) and the mixture was stirred under a hydrogen atmosphere until no hydrogen was absorbed. After the removal of the catalyst by filtration, the solvent of the pale yellow filtrate was evaporated under reduced pressure to give a slightly reddish brown oil of the reduced product. It was confirmed from the NMR spectrum that this product was substantially pure 2-fluoro-4-chloro-5-methoxycarbonyloxy aniline. The aniline derivative obtained can be purified by column chromatography if necessary, and used as it is in the following reaction.

$^1$H-NMR (CDCl$_3$, TMS, ppm): δ 3.86(3H,s), 4.13(2H,br s), 6.48(1H,d,$J_{HF}$=8 Hz), 6.92(1H,d,$J_{HF}$=10 Hz)

REFERENCE EXAMPLE 7

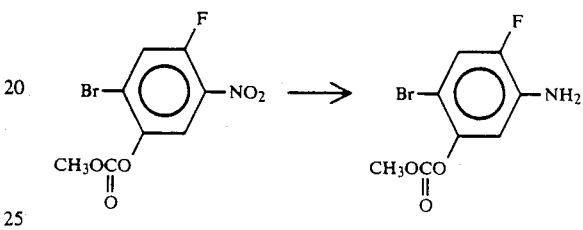

To an ethanol solution (300 ml) of 2-fluoro-4-bromo-5-methoxycarbonyloxy nitrobenzene (30.4 g, 0.1 mol) was added platinum dioxide (1.0 g) and the mixture was stirred under a hydrogen atmosphere until no hydrogen was absorbed. After the removal of the catalyst by filtration, the solvent of the filtrate was evaporated under reduced pressure to give a brown solid (28.0 g) of 2-fluoro-4-bromo-5-methoxycarbonyloxy aniline.

$^1$H-NMR (CCl$_4$, TMS, ppm): δ 3.83(3H,s), 5.01(2H,br s), 6.63(1H,d,$J_{HF}$=7.6 Hz), 7.06(1H,d,$J_{HF}$=9.8 Hz)

REFERENCE EXAMPLE 8

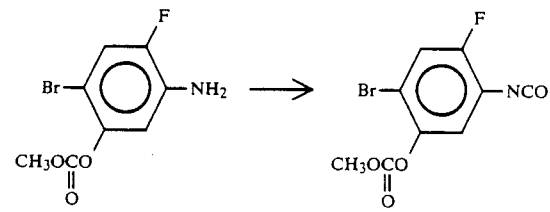

An ethyl acetate solution (150 ml) of trichloromethyl chloroformate (15 ml, 125 mmol) was placed in a 500 ml three-necked flask fitted with a dropping funnel and a distillation apparatus. An ethyl acetate solution of 2-fluoro-4-bromo-5-methoxycarbonyloxy aniline (28.0 g, 113 mmol), which was synthesized by the method shown in Reference Example 4, was added dropwise into the solution in 20 minutes. After the addition, the mixture was heated at 80° C. so as to remove ethyl acetate by distillation. The reaction mixture was cooled by being allowed to stand and carbon tetrachloride (150 ml) was added thereto. The precipitate deposited was filtered off and then the solvent was removed under reduced pressure from the filtrate to give 2-fluoro-4-bromo-5-methoxycarbonyloxyphenyl isocyanate. (29.1 g, 94% yield)

$^1$H-NMR (CCl$_4$, TMS, ppm): δ 3.87(3H,s), 6.89(1H,d, $J_{HF}$=6.8 Hz), 7.31(1H,d,$J_{HF}$=8.6 Hz).

IR (KBr disk, cm$^{-1}$) 2260, 1770.

REFERENCE EXAMPLE 9

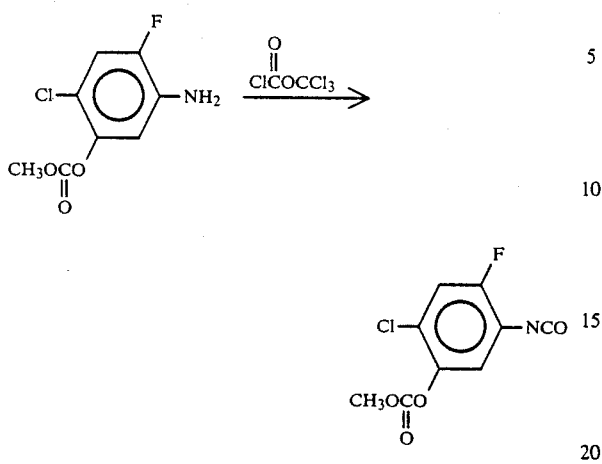

2-Fluoro-4-chloro-5-methoxycarbonyloxyphenyl isocyanate (20.6 g; yield, 84%) which was synthesized by the method shown in Reference Example 3 was obtained from 2-fluoro-4-chloro-5-methoxycarbonyloxy aniline (21.9 g, 10 mmol) and trichloromethyl chloroformate (19 ml) by an operation similar to that of Reference Example 7.

$^1$H-NMR (CDCl$_3$, TMS, ppm): δ  3.88(3H,s), 6.97(1H,d), 7.37(1H,d).

IR (KBr disk, cm$^{-1}$): 2260, 1770.

REFERENCE EXAMPLE 10

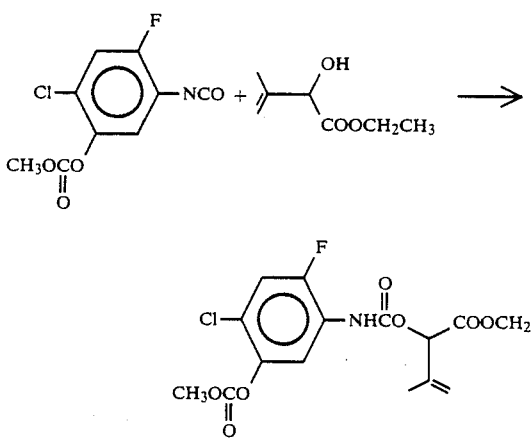

To a benzene solution (50 ml) of a mixture of ethyl 2-hydroxy-3-methyl-3-butenoate (1.44 g, 10 mmol) and 2-fluoro-4-chloro-5-methoxycarbonyloxyphenyl isocyanate (2.45 g, 10 mmol) which was synthesized in Reference Examples 6 and 9, was added a catalytic amount of triethylamine and the mixture was stirred for 0.5 hours at room temperature. After the reaction was completed, the resulting mixture was washed with 1N hydrochloric acid, and then the organic layer was dried and concentrated under reduced pressure. The slightly yellow oil obtained was purified using a silica gel column to give (1'-ethoxycarbonyl)methallyl N-(2-fluoro-4-chloro-5-methoxycarbonyloxyphenyl)carbonate. (85% yield)

$^1$H-NMR (CDCl$_3$, TMS, ppm): δ  1.29(3H,t), 1.84(3H,br s), 3.93(3H,s), 4.24(2H,q), 5.14(1H,m), 5.23(1H,m), 5.45(1H,s), 7.20(1H,d), 7.0–7.35(1H,br s), 8.10(1H,d).

REFERENCE EXAMPLE 11

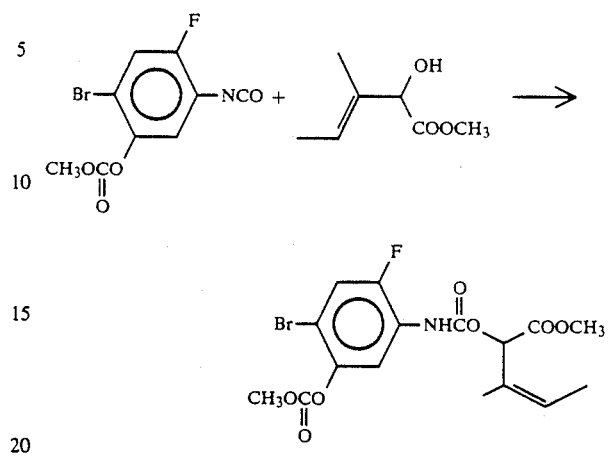

A benzene solution (50 ml) of a mixture of a small excess methyl 2-hydroxy-3-methyl-3-pentenoate and 2-fluoro-4-bromo-5-methoxycarbonyloxyphenyl isocyanate (2.74 g, 9.5 mmol), which was synthesized by the method shown in Reference Examples 7 and 8, was heated at reflux for 1 hour. After the reaction was completed, the resulting mixture was washed with 1N hydrochloric acid, and then the organic layer was dried and concentrated under reduced pressure. The oily product was purified using a silica gel column to give 1'-methoxycarbonyl-2'-methyl-2'-butenyl N-(2-fluoro-4-bromo-5-methoxycarbonyloxyphenyl)carbonate. (2.47 g, 57% yield)

$^1$H-NMR (CCl$_4$, TMS, ppm): δ  1.67(3H,s), 1.70(3H,d), 3.70(3H,s), 3.87(3H,s), 5.27(1H,s), 5.68(1H,m), 7.0(1H,br s), 7.27(1H,d), 8.03(1H,d).

EXAMPLE 12

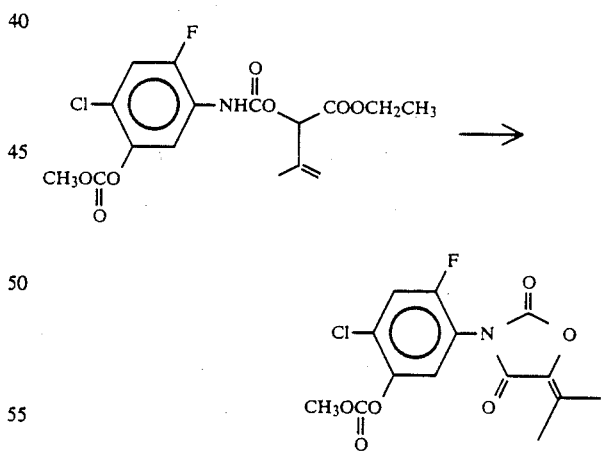

A benzene solution (20 ml) of (1'-ethoxycarbonyl)methallyl N-(2-fluoro-4-chloro-5-methoxycarbonyloxyphenyl)carbonate (1.95 g, 5.0 mmol), which was synthesized by the method shown in Reference Example 6, 9 or 10, was refluxed for 12 hours in the presence of a catalytic amount of sodium acetate. After the reaction was completed, the resulting mixture was washed with 1N hydrochloric acid, and then the organic layer was dried and concentrated under reduced pressure. The oily product obtained was purified using a silica gel column to give 3-(2'-fluoro-4'-chloro-5'-methoxycarbonyloxyphenyl)-5-isopropylidene-1,3-oxazolidine-2,4-dione (1.27 g, 74% yield)

$^1$H-NMR (CDCl$_3$, TMS, ppm): δ 2.05(3H,s), 2.28(3H,s), 3.95(3H,s), 7.32(d,1H), 7.42( H,d).

TABLE 4

Physical and Analytical Data for Oxazolidinedione Derivatives

| Compound No.[1] | m.p. (°C.) | Formula | C (%) Found (Calculated) | H (%) | N (%) | IR (cm$^{-1}$) |
|---|---|---|---|---|---|---|
| 30 | 143.5–145.5 | C$_{15}$H$_{11}$Cl$_2$NO$_4$ | 52.87 (52.96) | 3.14 (3.25) | 4.07 (4.12) | 2140, 1804, 1740, 1685 |
| 31* | 102–103.5 | C$_{16}$H$_{13}$Cl$_2$NO$_4$ | 53.80 (54.26) | 3.62 (3.70) | 3.89 (3.95) | 2150, 1813, 1743, 1685 |
| 32 | 134–135.5 | C$_{15}$H$_{11}$ClFNO$_4$ | 55.14 (55.66) | 3.30 (3.43) | 4.27 (4.33) | 2180, 1815, 1742, 1692 |
| 33* | 82–87.5 | C$_{16}$H$_{13}$ClFNO$_4$ | 56.67 (56.90) | 3.85 (3.85) | 4.09 (4.15) | 2130, 1815, 1740, 1680 |
| 34 | 140–142.5 | C$_{15}$H$_{11}$BrFNO$_4$ | 48.65 (48.94) | 2.89 (3.01) | 3.78 (3.80) | 2140, 1815, 1741, 1690 |
| 35* | 96–98 | C$_{16}$H$_{13}$BrFNO$_4$ | 49.58 (50.28) | 3.43 (3.43) | 3.62 (3.67) | 2140, 1815, 1740, 1680 |
| 36 | 94–100 | C$_{16}$H$_{13}$ClFNO$_4$ | 56.43 (56.90) | 3.78 (3.88) | 4.09 (4.15) | 2120, 1820, 1736, 1680 |
| 37 | 110–111.5 | C$_{17}$H$_{15}$ClFNO$_4$ | 58.03 (58.05) | 4.28 (4.30) | 3.85 (3.98) | 2200, 1820, 1740, 1685 |
| 38 | 100–102 | C$_{17}$H$_{15}$Cl$_2$NO$_4$ | 55.33 (55.45) | 4.24 (4.11) | 3.58 (3.80) | 2250, 1820, 1745, 1690 |
| 39 | 68.5–69.5 | C$_{15}$H$_{13}$ClFNO$_4$ | 55.28 (55.31) | 4.08 (4.02) | 4.25 (4.30) | 1820, 1750, 1695 |
| 40* | 95.5–100.5 | C$_{16}$H$_{15}$BrFNO$_4$ | 49.82 (50.02) | 3.84 (3.94) | 3.63 (3.65) | 1814, 1740, 1687 |
| 41 | 98–100 | C$_{17}$H$_{17}$ClFNO$_4$ | 57.36 (57.72) | 4.82 (4.84) | 3.75 (3.96) | 1815, 1740, 1686 |
| 42 | 93–96 | C$_{16}$H$_{15}$Cl$_2$NO$_4$ | 53.65 (53.95) | 4.40 (4.24) | 3.79 (3.93) | 1830, 1740, 1695 |
| 43* | glassy mass | C$_{16}$H$_{14}$BrClFNO$_4$ | 45.81 (45.90) | 3.18 (3.37) | 3.13' (3.35) | 1816, 1740, 1680 |
| 44 | 87–88 | C$_{15}$H$_{12}$Cl$_2$FNO$_4$ | 50.03 (50.02) | 3.54 (3.36) | 3.55 (3.89) | 1820, 1750, 1695 |
| 45 | 96–102 | C$_{16}$H$_{14}$BrClFNO$_4$ | 45.68 (45.90) | 3.28 (3.37) | 3.25 (3.35) | 1830, 1740, 1690 |
| 46 | 132.5–139 | C$_{17}$H$_{17}$ClFNO$_6$ | 53.08 (52.93) | 4.14 (4.44) | 3.43 (3.63) | 1815, 1740, 1694 |
| 47* | 101–103 | C$_{18}$H$_{19}$ClFNO$_6$ | 54.31 (54.08) | 4.85 (4.79) | 3.68 (3.50) | 1820, 1743, 1690 |
| 48 | 135.5–136.5 | C$_{17}$H$_{17}$Cl$_2$FNO$_6$ | 50.41 (50.76) | 4.13 (4.26) | 3.46 (3.48) | 1815, 1745, 1690 |
| 49* | 103–105.5 | C$_{18}$H$_{19}$Cl$_2$NO$_6$ | 51.28 (51.94) | 4.72 (4.60) | 3.46 (3.36) | 1814, 1749, 1686 |
| 50 | oil | C$_{22}$H$_{27}$Cl$_2$NO$_6$ | 55.71 (55.94) | 5.42 (5.76) | 2.89 (2.97) | 1820, 1740, 1690 |
| 51* | 104–108 | C$_{14}$H$_{13}$Cl$_2$NO$_4$ | 50.41 (50.93) | 3.85 (3.97) | 4.16 (4.24) | 1820, 1745, 1680 |
| 52 | 97–99 | C$_{13}$H$_{11}$ClFNO$_4$ | 52.16 (52.10) | 3.80 (3.70) | 4.58 (4.67) | 1820, 1740, 1695 |
| 53* | 81–85 | C$_{16}$H$_{17}$ClFNO$_4$ | 56.41 (56.23) | 5.13 (5.01) | 4.03' (4.10) | 1815, 1743, 1680 |
| 54* | 102–104.5 | C$_{16}$H$_{17}$BrNO$_4$ | 49.14 (49.76) | 4.29 (4.44) | 3.48 (3.63) | 1815, 1740, 1685 |
| 55 | 98–99.5 | C$_{17}$H$_{17}$ClFNO$_4$ | 57.56 (57.72) | 4.74 (4.84) | 3.88 (3.96) | 1820, 1743, 1693 |
| 56 | 73–75 | C$_{18}$H$_{19}$ClFNO$_4$ | 58.46 (58.78) | 5.02 (5.21) | 3.74 (3.81) | 1820, 1750, 1695 |

[1]The compounds asterisked are mixtures of cis and trans isomers with respect to the stereochemistry of the double bonds at the 5-positions of the oxazolidinedione rings.

TABLE 5

$^1$H-NMR Spectral Data for Oxazolidinedione Derivatives

| Compound No.[1] | $^1$H-NMR (CDCl$_3$, TMS, δ ppm) |
|---|---|
| 30 | 2.06(3H,s), 2.30(3H,s), 2.57(1H,t), 4.77(2H,d), 7.03(1H,s), 7.59(1H,s) |
| 31* | 1.16(3H,dt), 2.05 and 2.26(total 3H, each s), 2.43 and 2.75(total 2H, each q), 2.61(1H,t), 4.76(2H,d), 7.06(1H,s), 7.58(1H,s) |
| 32 | 2.06(3H,s), 2.29(3H,s), 2.58(1H,t), 4.77(2H,d), 7.07(1H,d), 7.36(1H,d) |
| 33* | 1.15(3H,t), 2.03 and 2.26(total 3H, each s), 2.41 and 2.75(total 2H, each q), 2.58(1H,t), 4.74(2H,d), 7.08(1H,d), 7.35(1H,d) |
| 34 | 2.03(3H,s), 2.27(3H,s), 2.57(1H,t), 4.73(2H,d), 7.00(1H,d), 7.47(1H,d) |
| 35* | 1.16(3H,t), 2.03 and 2.24(total 3H, each s), 2.41 and 2.76(total 2H, each q), 2.58(1H,t), 4.75(2H,d,) 7.03(1H,d), 7.50(1H,d) |
| 36 | 1.70(3H,t), 2.03(3H,s), 2.28(3H,s), 2.52(1H,d), 4.80(1H,m), 7.08(1H,d), 7.28(1H,d) |
| 37 | 1.77(3H,t), 2.04(3H,s), 2.27(3H,s), 2.63(2H,tq), 4.05(2H,t), 6.82(1H,d), 7.35(1H,d) |
| 38 | 1.74(3H,t), 2.04(3H,s), 2.26(3H,s), 2.63(2H,tq), 4.05(2H,t), 6.80(1H,s), 7.52(1H,s) |

TABLE 5-continued $^1$H-NMR Spectral Data for Oxazolidinedione Derivatives

| Compound No.$^1$ | $^1$H-NMR (CDCl$_3$, TMS, δ ppm) |
|---|---|
| 39 | 2.04(3H,s), 2.29(3H,s), 4.56(2H,m), 5.27(1H,m), 5.43(1H,m), 5.99(1H,m), 6.83(1H,d), 7.28(1H,d) |
| 40* | 1.13(3H,t), 2.02 and 2.25(total 3H, each s), 2.40 and 2.73(total 2H, each q), 4.55(2H,ddd), 5.28(1H,tdd), 5.42(1H,tdd), 6.02(1H,tdd), 6.80(1H,d), 7.47(1H,d) |
| 41 | 1.77(3H,br s), 2.02(3H,s), 2.27(3H,s), 2.50(2H,td), 4.07(2H,t), 4.80(2H,m), 6.87(1H,d), 7.28(1H,d) |
| 42 | 1.83(3H,s), 2.04(3H,s), 2.27(3H,s), 4.46(2H,s), 5.03(1H,s), 5.11(1H,s), 6.81(1H,s), 7.56(1H,s) |
| 43* | 1.15(3H,t), 1.99 and 2.20(total 3H, each s), 2.37 and 2.70(total 2H, each q), 4.50(2H,dd), 6.07(1H,dt), 6.43(1H,dt), 6.76(1H,dt), 7.43(1H,d) |
| 44 | 2.04(3H,s), 2.27(3H,s), 4.60(2H,dd), 5.49(1H,m), 5.68(1H,m), 6.83(1H,d), 7.35(1H,d) |
| 45 | 1.78(3H,d), 2.03(3H,s), 2.27(3H,s), 4.67(2H,br s), 6.20(1H,qt), 6.85(1H,d), 7.30(1H,d) |
| 46 | 1.24(3H,t), 1.65(3H,d), 2.03(3H,s), 2.28(3H,s), 4.20(2H,q), 4.68(1H,q), 6.87(1H,d), 7.32(1H,d) |
| 47* | 1.14(3H,s), 1.24(3H,t), 1.66(3H,d), 2.02 and 2.25(total 3H, each s), 2.41 and 2.74(total 2H, each q), 4.21(2H,q), 4.68(1H,q), 6.89(1H,d), 7.33(1H,d) |
| 48 | 1.23(3H,t), 1.67(3H,d), 2.06(3H,s), 2.28(3H,s), 4.19(2H,q), 4.70(1H,q), 6.80(1H,d), 7.58(1H,s) |
| 49* | 1.15(3H,t), 1.21(3H,t), 1.65(3H,d), 2.01 and 2.25(total 3H, each t), 2.41 and 2.75(total 2H, each q), 4.18(2H,q), 4.73(1H,q), 6.79(1H,d), 7.56(1H,s) |
| 50 | 0.67–1.02(6H,m), 1.02–1.67(9H,m), 2.01(3H,s), 2.22(3H,s), 3.97(2H,d), 4.63(2H,s), 6.80(1H,s), 7.52(1H,s) |
| 51* | 1.15(3H,t), 2.05 and 2.27(total 3H, each s), 2.43 and 2.75(total 2H, each q), 3.90(3H,s), 6.85(1H,d), 7.57(1H,d) |
| 52 | 2.08(3H,s), 2.32(3H,s), 3.92(3H,s), 6.91(1H,d), 7.36(1H,d) |
| 53* | 1.15(3H,t), 1.37(6H,d), 2.03 and 2.25 (total 3H, each s), 2.40 and 2.73 (total 2H, each q), 4.41(1H,sept), 6.85(1H,d), 7.27(1H,d) |
| 54* | 1.15(3H,t), 1.38(6H,d), 2.03 and 2.27 (total 3H, each s), 2.42 and 2.75 (total 2H, each q), 4.43(1H,sept), 6.85(1H,d), 7.48(1H,d) |
| 55 | 1.58–1.91(8H,m), 2.00(3H,s), 2.26(3H,s), 4.73(1H,m), 6.77(1H,d), 7.27(1H,d) |
| 56 | 1.17–1.96(10H,m), 2.04(3H,s), 2.28(3H,s), 4.2(1H,m), 6.82(1H,d), 7.26(1H,d) |

$^1$The compounds asterisked are mixtures of cis and trans isomers with respect to the stereochemistry of the double bonds at the 5-positions of the oxazolidinedione rings.

The compounds of the present invention which can be obtained by the methods described in the examples have excellent qualities as herbicides, as described above.

When the compounds of the present invention are used as herbicides, although they can be applied as they are, they generally used as herbicides of the present invention in mixtures with one or more adjuvants. In general, it is preferable to use herbicides to which various carriers, fillers, solvents, surfactants or stabilizers have been added as adjuvants and which are prepared in such forms as wettable powder, emulsion, powder, or granules.

Suitable examples of solvents which are adjuvants include water, alcohols, ketones, ethers, aliphatic and aromatic hydrocarbons, halogenated hydrocarbons, acid amides, esters, and nitriles and mixtures of one or more kinds of these solvents may be used.

Preferable examples of the fillers include clay in such forms as kaoline and bentonite, a kind of talc such as talc and pyrophyllite, mineral powders of oxides such as diatomaceous earth and white carbon, and plant powders such as soybean powder and CMC, mixtures of one or more kinds of fillers may be used.

The surfactants may be used in the form of a spreader, a dispersant, an emulsifier, or a penetrant. Examples of surfactants include nonionic surfactants, cationic surfactants, anionic surfactants, and amphoteric surfactants. These surfactants are employed in mixtures of one or more kinds, depending upon the uses intended.

Preferable methods of applying the herbicides of the present invention include soil treatments, water-surface treatments and treatments of stalk and leaves, and the herbicides exhibit an excellent effect particularly when applied during the time before the germination of the weeds to be controlled to the plumule thereof.

The herbicides of the present invention can be applied in mixture with or combination with other active ingredients which do not inhibit the weed-killing activity of the effective ingredients of the herbicides, for example, other herbicides, insecticides, fungicides, or plant growth regulators.

The present invention will be described in detail below by way of examples of preparation of the herbicides of the present invention and experimental examples of the weed-killing effect of the herbicides, but the invention is not limited to these examples. "Parts" indicates "parts by weight".

Preparation Example 1 (Emulsion)

Twenty parts of each of the compounds of the present invention, 75 parts of xylene and 5 parts of Solpole 900 A (produced by Toho Chemical Co., Ltd.) were uniformly mixed to form an emulsion.

Preparation Example 2 (Water-dispersible powder)

Fifty parts of each of the compounds of the present invention, 25 parts of diatomaceous earth, 22 parts of clay and 3 parts of Lunox RIOO C (produced by Toho Chemical Co., Ltd.) were uniformly mixed and ground to form water-despersible powder.

Preparation Example 3 (Granules)

Five parts of each of the compounds of the present invention, 35 parts of bentonite, 55 parts of talc and 5 parts of sodium lignin sulfonate were uniformly mixed and ground and water was then added to the mixture which was then kneaded, granulated by an extrusion granulator, dried, and graded to form granules.

Experimental Example 1 (Effect on weeds in paddy fields)

Wagner pots each having an area of 1/5,000 are were filled with soil from a paddy field in which the seeds of *Echinochloa Crus-galli* var., *Monochoria vaginalis* var., *Ammannia multiflora* Roxb. and paddy seedings (grade: Nihonbare) of a 3–4 leaf time were respectively sown or transplanted. The pots were filled with water and kept in that state. After 5 days, the water surface in each pot was treated with given amounts of each herbicide of the present invention, which had been formed as granules in accordance with Preparation Example 3, in such doses that the effective ingredients thereof reached ratio of 50, 25, 20, 10, 12.5 and 5 g per are, respectively. After 30 days had passed from the treatment with the granules, the weed-killing effect on the plants and the phytotoxicity of the paddy were examined on the basis of the following criteria. The results obtained are shown in Table 6.

| Criteria | |
|---|---|
| Degree of weed-killing | Ratio of remaining weeds (%) |
| 0 | 81–100 |
| 1 | 61–80 |
| 2 | 41–60 |
| 3 | 21–40 |
| 4 | 6–20 |
| 5 | 0–5 |
| Phytotoxicity | |
| − | No damage |
| + | Slight damage |
| ++ | Small damage |
| +++ | Medium damage |
| ++++ | Heavy damage |
| x | Dead |

TABLE 6

| Test Compound | Applied amount (g/a) | Degree of weed-killing Echinochloa Crus-galli var. | Monochoria vaginalis var. | Ammannia multiflora Roxb. | Phytotoxicity Rice plant |
|---|---|---|---|---|---|
| 1 | 50 | 4 | 4 | 4 | − |
| | 25 | 4 | 3 | 3 | − |
| | 12.5 | 3 | 2 | 2 | − |
| 4 | 50 | 5 | 5 | 5 | − |
| | 25 | 5 | 5 | 5 | − |
| | 12.5 | 5 | 5 | 5 | − |
| 5 | 50 | 4 | 5 | 5 | − |
| | 25 | 3 | 5 | 5 | − |
| | 12.5 | 3 | 5 | 5 | − |
| 6 | 50 | 4 | 5 | 5 | − |
| | 25 | 3 | 5 | 5 | − |
| | 12.5 | 2 | 5 | 5 | − |
| 7 | 50 | 5 | 5 | 5 | − |
| | 25 | 5 | 5 | 5 | − |
| | 12.5 | 5 | 5 | 5 | − |
| 9 | 50 | 4 | 5 | 5 | − |
| | 25 | 4 | 5 | 5 | − |
| | 12.5 | 3 | 5 | 5 | − |
| 14 | 50 | 5 | 5 | 5 | − |
| | 25 | 4 | 5 | 4 | − |
| | 12.5 | 4 | 4 | 3 | − |
| 15 | 50 | 4 | 4 | 4 | − |
| | 25 | 3 | 3 | 3 | − |
| | 12.5 | 3 | 2 | 3 | − |
| 16 | 50 | 5 | 5 | 5 | − |
| | 25 | 5 | 5 | 5 | − |
| | 12.5 | 4 | 5 | 4 | − |
| 24 | 50 | 5 | 5 | 5 | − |
| | 25 | 4 | 5 | 4 | − |
| | 12.5 | 3 | 5 | 3 | − |
| 26 | 50 | 5 | 5 | 5 | − |
| | 25 | 5 | 5 | 5 | − |
| | 20 | 5 | 5 | 5 | − |
| | 10 | 5 | 5 | 5 | − |
| | 12.5 | 5 | 5 | 5 | − |
| | 5 | 3 | 5 | 4 | − |
| 27 | 50 | 5 | 5 | 5 | − |
| | 25 | 5 | 5 | 5 | − |
| | 20 | 5 | 5 | 5 | ++ |
| | 10 | 5 | 5 | 5 | + |
| | 12.5 | 5 | 5 | 5 | − |
| | 5 | 5 | 5 | 5 | − |
| 30 | 20 | 5 | 5 | 5 | + |
| | 10 | 5 | 5 | 5 | + |
| | 5 | 4 | 5 | 5 | − |
| 31 | 20 | 5 | 5 | 5 | ++ |
| | 10 | 5 | 5 | 5 | + |
| | 5 | 4 | 5 | 5 | − |
| 32 | 20 | 5 | 5 | 5 | ++ |
| | 10 | 5 | 5 | 5 | + |
| | 5 | 5 | 5 | 5 | − |
| 33 | 20 | 5 | 5 | 5 | ++ |
| | 10 | 5 | 5 | 5 | + |
| | 5 | 4 | 5 | 5 | − |
| 34 | 20 | 5 | 5 | 5 | +++ |
| | 10 | 5 | 5 | 5 | ++ |
| | 5 | 5 | 5 | 5 | + |
| 35 | 20 | 5 | 5 | 5 | ++ |
| | 10 | 5 | 5 | 5 | + |

TABLE 6-continued

| Test Compound | Applied amount (g/a) | Degree of weed-killing | | | Phytotoxicity Rice plant |
|---|---|---|---|---|---|
| | | Echinochloa Crus-galli var. | Monochoria vaginalis var. | Ammannia multiflora Roxb. | |
| 36 | 5 | 4 | 5 | 5 | — |
| | 20 | 5 | 5 | 5 | +++ |
| | 10 | 5 | 5 | 5 | ++ |
| 37 | 5 | 5 | 5 | 5 | — |
| | 20 | 5 | 5 | 5 | + |
| | 10 | 5 | 5 | 5 | — |
| 38 | 5 | 5 | 5 | 5 | — |
| | 20 | 5 | 5 | 5 | — |
| | 10 | 3 | 5 | 4 | — |
| | 5 | 2 | 5 | 4 | — |
| 39 | 20 | 5 | 5 | 5 | ++ |
| | 10 | 5 | 5 | 5 | + |
| | 5 | 4 | 5 | 5 | — |
| 40 | 20 | 5 | 5 | 5 | ++ |
| | 10 | 5 | 5 | 5 | + |
| | 5 | 4 | 5 | 5 | — |
| 41 | 20 | 5 | 5 | 5 | — |
| | 10 | 4 | 5 | 4 | — |
| | 5 | 3 | 5 | 4 | — |
| 42 | 20 | 5 | 5 | 5 | — |
| | 10 | 4 | 5 | 4 | — |
| | 5 | 2 | 5 | 3 | — |
| 43 | 20 | 5 | 5 | 5 | + |
| | 10 | 5 | 5 | 5 | — |
| | 5 | 5 | 5 | 5 | — |
| 44 | 20 | 5 | 5 | 5 | — |
| | 10 | 4 | 5 | 5 | — |
| | 5 | 3 | 5 | 4 | — |
| 45 | 20 | 5 | 5 | 5 | — |
| | 10 | 3 | 5 | 4 | — |
| | 5 | 2 | 5 | 3 | — |
| 46 | 20 | 5 | 5 | 5 | — |
| | 10 | 4 | 5 | 5 | — |
| | 5 | 3 | 5 | 4 | — |
| 47 | 20 | 5 | 5 | 5 | — |
| | 10 | 5 | 5 | 5 | — |
| | 5 | 3 | 5 | 3 | — |
| 48 | 20 | 5 | 5 | 5 | — |
| | 10 | 3 | 5 | 4 | — |
| | 5 | 2 | 5 | 3 | — |
| 49 | 20 | 5 | 5 | 5 | — |
| | 10 | 4 | 3 | 3 | — |
| | 5 | 2 | 2 | 1 | — |
| 50 | 20 | 3 | 5 | 5 | — |
| | 10 | 2 | 4 | 3 | — |
| | 5 | 1 | 2 | 1 | — |
| 51 | 20 | 5 | 5 | 5 | + |
| | 10 | 5 | 5 | 5 | — |
| | 5 | 4 | 5 | 5 | — |
| 52 | 20 | 5 | 5 | 5 | + |
| | 10 | 5 | 5 | 5 | — |
| | 5 | 5 | 5 | 5 | — |
| 53 | 20 | 5 | 5 | 5 | — |
| | 10 | 5 | 5 | 5 | — |
| | 5 | 4 | 5 | 5 | — |
| 54 | 20 | 5 | 5 | 5 | ++ |
| | 10 | 5 | 5 | 5 | + |
| | 5 | 5 | 5 | 5 | — |
| 55 | 20 | 5 | 5 | 5 | — |
| | 10 | 5 | 5 | 5 | — |
| | 5 | 5 | 5 | 5 | — |
| 56 | 20 | 5 | 5 | 5 | + |
| | 10 | 5 | 5 | 5 | — |
| | 5 | 3 | 5 | 4 | — |
| Reference MO | 20 | 5 | 5 | 5 | + |
| | 10 | 4 | 5 | 5 | — |
| | 5 | 3 | 4 | 4 | — |

Reference MO: 2,4,6-trichlorophenyl 4-nitrophenyl ether

Experimental Example 2

Wagner pots each having an area of 1/5,000 are were filled with soil from a plowed field and seeds of *Digitaria sanguinalis* Scopoli, *Polygonum caespitosum* var. and *Amaranthus lividus* L. were sown as weeds, as well as seeds of corn, cotton and soybean as crops. The seeds were covered with the soil to a height of 1 cm. On the next day, a diluted solution of each of the water-dispersible powders described in Preparation Example 2 was uniformly sprayed over the soil covering the seeds. After 20 days had passed from this treatment, the weed killing effect and phytotoxicity were examined in a manner similar to that in Experimental Example 1. The results are shown in Table 7.

TABLE 7

| Test Compound | Applied amount (g/a) | Degree of weed-killing | | | Phytotoxicity | |
|---|---|---|---|---|---|---|
| | | *Digitaria sanguinalis* Scopoli | *Polygonum caespitosum* var. | *Amaranthus lividus* L. | Corn | Cotton |
| 1 | 50 | 4 | 3 | 4 | — | — |
| | 25 | 3 | 3 | 3 | — | — |
| | 12.5 | 2 | 2 | 2 | — | — |
| 4 | 50 | 5 | 5 | 5 | — | — |
| | 25 | 5 | 5 | 5 | — | — |
| | 12.5 | 5 | 5 | 5 | — | — |
| 5 | 50 | 4 | 4 | 4 | — | — |
| | 25 | 3 | 3 | 3 | — | — |
| | 1.25 | 2 | 2 | 3 | — | — |
| 6 | 50 | 3 | 3 | 3 | — | — |
| | 25 | 2 | 2 | 2 | — | — |
| | 12.5 | 1 | 1 | 2 | — | — |
| 7 | 50 | 5 | 5 | 5 | — | — |
| | 12.5 | 4 | 3 | 4 | — | — |
| 9 | 50 | 5 | 5 | 5 | — | — |
| | 25 | 4 | 4 | 4 | — | — |
| | 12.5 | 3 | 3 | 4 | — | — |
| 14 | 50 | 4 | 4 | 5 | — | — |
| | 25 | 3 | 3 | 4 | — | — |
| | 12.5 | 3 | 3 | 3 | — | — |
| 15 | 50 | 3 | 3 | 3 | — | — |
| | 25 | 2 | 2 | 2 | — | — |
| | 12.5 | 1 | 2 | 2 | — | — |
| 16 | 50 | 5 | 5 | 5 | — | — |
| | 25 | 5 | 5 | 5 | — | — |
| | 12.5 | 4 | 5 | 5 | — | — |
| 24 | 50 | 4 | 4 | 5 | — | — |
| | 25 | 3 | 3 | 3 | — | — |
| | 12.5 | 3 | 3 | 3 | — | — |
| 26 | 50 | 5 | 5 | 5 | — | — |
| | 25 | 5 | 5 | 5 | — | — |
| | 20 | 5 | 5 | 5 | — | — |
| | 12.5 | 5 | 5 | 5 | — | — |
| | 10 | 4 | 4 | 5 | — | — |
| | 5 | 3 | 2 | 4 | — | — |
| 27 | 50 | 5 | 5 | 5 | — | — |
| | 25 | 5 | 5 | 5 | — | — |
| | 20 | 5 | 5 | 5 | — | — |
| | 12.5 | 5 | 5 | 5 | — | — |
| | 10 | 5 | 5 | 5 | — | — |
| | 5 | 5 | 5 | 5 | — | — |

| Test Compound | Applied amount (g/a) | Degree of weed-killing | | | Phytotoxicity |
|---|---|---|---|---|---|
| | | *Digitaria sanguinal* Scopoli | *Chenopodium album* L. | *Amaranthus lividus* L. | Soybean |
| 30 | 20 | 5 | 5 | 5 | — |
| | 10 | 5 | 5 | 5 | — |
| | 5 | 4 | 4 | 5 | — |
| 31 | 20 | 5 | 5 | 5 | + |
| | 10 | 5 | 5 | 5 | — |
| | 5 | 4 | 5 | 5 | — |
| 32 | 20 | 5 | 5 | 5 | — |
| | 10 | 5 | 5 | 5 | + |
| | 5 | 5 | 5 | 5 | — |
| 33 | 20 | 5 | 5 | 5 | + |
| | 10 | 5 | 5 | 5 | — |
| | 5 | 4 | 4 | 5 | — |
| 34 | 20 | 5 | 5 | 5 | + |
| | 10 | 5 | 5 | 5 | + |
| | 5 | 5 | 5 | 5 | — |
| 35 | 20 | 5 | 5 | 5 | + |
| | 10 | 5 | 5 | 5 | — |
| | 5 | 5 | 5 | 5 | — |
| 36 | 20 | 5 | 5 | 5 | ++ |
| | 10 | 5 | 5 | 5 | + |
| | 5 | 5 | 5 | 5 | — |
| 37 | 20 | 5 | 5 | 5 | — |
| | 10 | 5 | 5 | 5 | — |
| | 5 | 3 | 4 | 5 | — |

TABLE 7-continued

| Compound | Applied | | | | Phytotoxicity |
|---|---|---|---|---|---|
| 38 | 20 | 4 | 4 | 4 | + |
|  | 10 | 3 | 3 | 3 | − |
|  | 5 | 2 | 1 | 2 | − |
| 39 | 20 | 5 | 5 | 5 | + |
|  | 10 | 5 | 5 | 5 | − |
|  | 5 | 4 | 5 | 5 | − |
| 40 | 20 | 5 | 5 | 5 | + |
|  | 10 | 5 | 5 | 5 | − |
|  | 5 | 4 | 5 | 5 | − |
| 41 | 20 | 5 | 4 | 5 | − |
|  | 10 | 3 | 3 | 4 | − |
|  | 5 | 1 | 2 | 3 | − |
| 42 | 20 | 4 | 4 | 4 | − |
|  | 10 | 2 | 3 | 3 | − |
|  | 5 | 1 | 2 | 2 | − |
| 43 | 20 | 5 | 5 | 5 | + |
|  | 10 | 4 | 4 | 5 | − |
|  | 5 | 3 | 3 | 4 | − |
| 44 | 20 | 5 | 5 | 5 | − |
|  | 10 | 3 | 4 | 4 | − |
|  | 5 | 2 | 3 | 3 | − |
| 45 | 20 | 5 | 4 | 4 | − |
|  | 10 | 3 | 3 | 3 | − |
|  | 5 | 1 | 1 | 2 | − |
| 46 | 20 | 5 | 5 | 5 | − |
|  | 10 | 4 | 4 | 5 | − |
|  | 5 | 3 | 3 | 4 | − |
| 47 | 20 | 4 | 4 | 5 | − |
|  | 10 | 2 | 3 | 4 | − |
|  | 5 | 1 | 2 | 3 | − |
| 48 | 20 | 4 | 4 5 | — | — |
|  | 10 | 2 | 3 | 5 | — |
|  | 5 | 1 | 2 | 3 | − |
| 49 | 20 | 4 | 4 | 4 | − |
|  | 10 | 2 | 3 | 4 | − |
|  | 5 | 1 | 2 | 3 | − |
| 50 | 20 | 3 | 4 | 4 | − |
|  | 10 | 2 | 3 | 3 | − |
|  | 5 | 1 | 1 | 1 | − |
| 51 | 20 | 5 | 5 | 5 | − |
|  | 10 | 5 | 5 | 5 | − |
|  | 5 | 4 | 4 | 5 | − |
| 52 | 20 | 5 | 5 | 5 | ++ |
|  | 10 | 5 | 5 | 5 | + |
|  | 5 | 4 | 5 | 5 | − |
| 53 | 20 | 5 | 5 | 5 | − |
|  | 10 | 5 | 5 | 5 | − |
|  | 5 | 4 | 5 | 5 | − |
| 54 | 20 | 5 | 5 | 5 | + |
|  | 10 | 5 | 5 | 5 | − |
|  | 5 | 5 | 5 | 5 | − |
| 55 | 20 | 5 | 5 | 5 | − |
|  | 10 | 4 | 5 | 5 | − |
|  | 5 | 3 | 4 | 5 | − |
| Reference MO 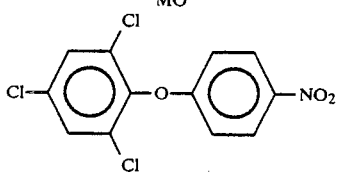 | 20 | 5 | 5 | 4 | +−− |
|  | 10 | 5 | 4 | 3 | |
|  | 5 | 4 | 3 | 2 | |

Experimental Example 3 (Effect of the treatment of stalk and leaves)

Wagner pots having an area of 1/5,000 are were filled with soil from a plowed field in which seeds of such weeds such as *Echinochloa Crus-galli* var., *Digitaria sanguinalis* Scopoli, *Polygonum caespitosum* var. *Amaranthus lividus* L. and *Chenopodium album* L. were sown. After 20 days, a chemical solution of a given concentration which was obtained by diluting with water the emulsion prepared from each of the compounds to be examined in accordance with Preparation Example 1 was uniformly sprayed on the stalks and the leaves of the weeds grown so that the amount of water dispersed was 100 1/10 a. Twenty days after from the treatment, the weed killing effect and the phytotoxicity (for wheat, soybean and corn) were evaluated in a manner similar to that of Experimental Example 1. The results obtained are shown in Table 8.

TABLE 8

| Applied | Degree of weed-killing |
|---|---|

TABLE 8-continued

| Test Compound | amount (ppm) | Echinochloa Crus-galli var. | Digitaria sanguinalis Scopoli | Polygomum caespitosum var. | Amaranthus lividus L. | Phytotoxicity Soybean |
|---|---|---|---|---|---|---|
| 1 | 2000 | 4 | 4 | 3 | 4 | — |
|   | 1000 | 3 | 3 | 2 | 3 | — |
|   | 500 | 2 | 2 | 2 | 2 | — |
| 4 | 2000 | 5 | 5 | 5 | 5 | + |
|   | 1000 | 5 | 5 | 5 | 5 | — |
|   | 500 | 4 | 4 | 4 | 4 | — |
| 5 | 2000 | 4 | 4 | 4 | 4 | — |
|   | 1000 | 4 | 4 | 3 | 4 | — |
|   | 500 | 3 | 3 | 3 | 3 | — |
| 6 | 2000 | 3 | 3 | 3 | 3 | — |
|   | 1000 | 2 | 2 | 2 | 2 | — |
|   | 500 | 2 | 2 | 2 | 2 | — |
| 7 | 2000 | 5 | 5 | 5 | 5 | — |
|   | 1000 | 4 | 5 | 5 | 4 | — |
|   | 500 | 3 | 4 | 4 | 4 | — |
| 9 | 2000 | 5 | 5 | 5 | 5 | — |
|   | 1000 | 4 | 4 | 4 | 4 | — |
|   | 500 | 3 | 3 | 3 | 3 | — |
| 14 | 2000 | 4 | 4 | 4 | 4 | — |
|   | 1000 | 3 | 4 | 3 | 3 | — |
|   | 500 | 2 | 3 | 2 | 2 | — |
| 15 | 2000 | 4 | 4 | 3 | 4 | — |
|   | 1000 | 3 | 3 | 3 | 3 | — |
|   | 500 | 2 | 2 | 1 | 2 | — |
| 16 | 2000 | 4 | 5 | 5 | 5 | — |
|   | 1000 | 3 | 4 | 5 | 5 | — |
|   | 500 | 3 | 3 | 4 | 4 | — |
| 24 | 2000 | 4 | 5 | 4 | 4 | — |
|   | 1000 | 4 | 4 | 3 | 3 | — |
|   | 500 | 3 | 4 | 3 | 3 | — |
| 26 | 2000 | 5 | 5 | 5 | 5 | — |
|   | 1000 | 5 | 5 | 5 | 5 | — |
|   | 500 | 4 | 4 | 4 | 4 | — |
| 27 | 2000 | 5 | 5 | 5 | 5 | — |
|   | 1000 | 5 | 5 | 5 | 5 | — |
|   | 500 | 4 | 4 | 4 | 5 | — |

| Test Compound | Applied amount (ppm) | Degree of weed-killing | | | Phytotoxicity Corn |
|---|---|---|---|---|---|
| | | Chenopodium album L. | Amaranthus lividus L. | Polygonum longisetum | |
| 30 | 2000 | 5 | 5 | 5 | ++ |
|   | 1000 | 5 | 5 | 5 | + |
|   | 500 | 4 | 5 | 5 | + |
| 31 | 2000 | 5 | 5 | 5 | ++ |
|   | 1000 | 5 | 5 | 5 | + |
|   | 500 | 5 | 4 | 4 | — |
| 32 | 2000 | 5 | 5 | 5 | + |
|   | 1000 | 5 | 5 | 5 | — |
|   | 500 | 4 | 5 | 4 | — |
| 33 | 2000 | 5 | 5 | 5 | ++ |
|   | 1000 | 5 | 5 | 5 | — |
|   | 500 | 5 | 5 | 5 | — |
| 34 | 2000 | 5 | 5 | 5 | +++ |
|   | 1000 | 5 | 5 | 5 | + |
|   | 500 | 5 | 5 | 5 | — |
| 35 | 2000 | 5 | 5 | 5 | +++ |
|   | 1000 | 5 | 5 | 5 | ++ |
|   | 500 | 5 | 5 | 5 | + |
| 36 | 2000 | 5 | 5 | 5 | +++ |
|   | 1000 | 5 | 5 | 5 | ++ |
|   | 500 | 5 | 5 | 5 | + |
| 37 | 2000 | 5 | 5 | 5 | + |
|   | 1000 | 5 | 5 | 5 | — |
|   | 500 | 4 | 5 | 5 | — |
| 38 | 2000 | 5 | 5 | 5 | + |
|   | 1000 | 3 | 5 | 4 | — |
|   | 500 | 2 | 4 | 3 | — |
| 39 | 2000 | 5 | 5 | 5 | ++ |
|   | 1000 | 5 | 5 | 5 | + |
|   | 500 | 5 | 5 | 5 | — |
| 40 | 2000 | 5 | 5 | 5 | ++ |
|   | 1000 | 5 | 5 | 5 | + |
|   | 500 | 5 | 5 | 5 | — |
| 41 | 2000 | 5 | 5 | 5 | + |
|   | 1000 | 5 | 5 | 5 | — |
|   | 500 | 3 | 4 | 4 | — |
| 42 | 2000 | 5 | 5 | 5 | + |
|   | 1000 | 3 | 4 | 4 | — |
|   | 500 | 1 | 3 | 2 | — |
| 43 | 2000 | 5 | 5 | 5 | + |

TABLE 8-continued
|  |  | 1000 | 5 | 5 | 5 | — |
|---|---|---|---|---|---|---|
|  |  | 500 | 4 | 4 | 3 | — |
| 44 |  | 2000 | 5 | 5 | 5 | + |
|  |  | 1000 | 4 | 4 | 3 | — |
|  |  | 500 | 3 | 2 | 2 | — |
| 45 |  | 2000 | 5 | 5 | 5 | + |
|  |  | 1000 | 3 | 4 | 4 | — |
|  |  | 500 | 1 | 2 | 2 | — |
| 46 |  | 2000 | 5 | 5 | 5 | + |
|  |  | 1000 | 3 | 3 | 3 | — |
|  |  | 500 | 2 | 1 | 2 | — |
| 47 |  | 2000 | 5 | 5 | 5 | + |
|  |  | 1000 | 4 | 4 | 3 | — |
|  |  | 500 | 3 | 2 | 2 | — |
| 48 |  | 2000 | 4 | 4 | 3 | — |
|  |  | 1000 | 3 | 4 | 2 | — |
|  |  | 500 | 2 | 3 | 2 | — |
| 49 |  | 2000 | 4 | 4 | 4 | — |
|  |  | 1000 | 2 | 2 | 3 | — |
|  |  | 500 | 1 | 1 | 1 | — |
| 50 |  | 2000 | 3 | 4 | 4 | — |
|  |  | 1000 | 2 | 2 | 2 | — |
|  |  | 500 | 1 | 1 | 1 | — |
| 51 |  | 2000 | 5 | 5 | 5 | — |
|  |  | 1000 | 5 | 5 | 5 | — |
|  |  | 500 | 4 | 5 | 5 | — |
| 52 |  | 2000 | 5 | 5 | 5 | ++ |
|  |  | 1000 | 5 | 5 | 5 | + |
|  |  | 500 | 4 | 5 | 5 | — |
| 53 |  | 2000 | 5 | 5 | 5 | +++ |
|  |  | 1000 | 5 | 5 | 5 | ++ |
|  |  | 500 | 5 | 5 | 5 | — |
| 54 |  | 2000 | 5 | 5 | 5 | +++ |
|  |  | 1000 | 5 | 5 | 5 | ++ |
|  |  | 500 | 5 | 5 | 5 | + |
| 55 |  | 2000 | 5 | 5 | 5 | + |
|  |  | 1000 | 4 | 5 | 5 | — |
|  |  | 500 | 3 | 5 | 5 | — |
| 56 |  | 2000 | 5 | 5 | 5 | + |
|  |  | 1000 | 4 | 4 | 5 | — |
|  |  | 500 | 3 | 2 | 3 | — |
| Reference MO | 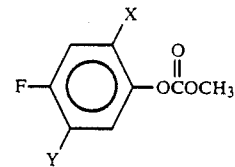 | 2000 | 5 | 5 | 5 | +++ |
|  |  | 1000 | 5 | 5 | 5 | ++ |
|  |  | 5000 | 5 | 5 | 5 | + |
We claim:
1. A compound of the formula
$$\underset{Y}{\underset{|}{\overset{X}{\underset{|}{\bigodot}}}}\text{F}\!\!-\!\!\bigodot\!\!-\!\!O\overset{O}{\overset{\|}{C}}CH_3$$
wherein X is a chlorine atom or a bromine atom and Y is an amino group or an isocyanato group.
* * * * *